US011833170B2

(12) United States Patent
Ralph et al.

(10) Patent No.: US 11,833,170 B2
(45) Date of Patent: Dec. 5, 2023

(54) ALTERING NET CHARGE ON MANNOSYLATED DEXTRANS TO MAXIMIZE TARGET TISSUE UPTAKE AND OFF TARGET COMPETITIVE BLOCKING

(71) Applicant: Navidea Biopharmaceuticals, Inc., Dublin, OH (US)

(72) Inventors: David A. Ralph, Columbus, OH (US); Jeffrey Scott Arnold, Andover, MA (US)

(73) Assignee: Navidea Biopharmaceuticals, Inc., Dublin, OH (US)

(*) Notice: Subject to any disclaimer, the term of this patent is extended or adjusted under 35 U.S.C. 154(b) by 0 days.

(21) Appl. No.: 18/164,296

(22) Filed: Feb. 3, 2023

(65) Prior Publication Data

US 2023/0248757 A1 Aug. 10, 2023

Related U.S. Application Data

(60) Provisional application No. 63/306,719, filed on Feb. 4, 2022.

(51) Int. Cl.

| | |
|---|---|
| ***A61K 31/721*** | (2006.01) |
| ***A61K 31/77*** | (2006.01) |
| ***A61K 31/80*** | (2006.01) |
| ***A61K 45/06*** | (2006.01) |

(52) U.S. Cl.

CPC .............. *A61K 31/77* (2013.01); *A61K 31/80* (2013.01); *A61K 45/06* (2013.01)

(58) Field of Classification Search

CPC ......... A61K 31/77; A61K 31/80; A61K 45/06

See application file for complete search history.

(56) References Cited

U.S. PATENT DOCUMENTS

| | | | | |
|---|---|---|---|---|
| 4,624,846 | A | 11/1986 | Goldenberg | |
| 6,409,990 | B1 * | 6/2002 | Vera | A61B 6/508 424/9.4 |
| 2008/0085871 | A1 | 4/2008 | Tam et al. | |
| 2014/0235790 | A1 * | 8/2014 | Stayton | A61K 47/58 525/54.3 |
| 2016/0206763 | A1 | 7/2016 | Cope | |
| 2019/0021608 | A1 | 1/2019 | Cope et al. | |
| 2019/0022259 | A1 | 1/2019 | Cope et al. | |
| 2021/0145989 | A1 * | 5/2021 | Ralph | A61K 47/61 |
| 2021/0275698 | A1 | 9/2021 | Cope | |

FOREIGN PATENT DOCUMENTS

| | | | |
|---|---|---|---|
| WO | 2015013341 | A1 | 1/2015 |
| WO | 2016011415 | A2 | 1/2016 |
| WO | 2016011419 | A1 | 1/2016 |
| WO | 2016118188 | A1 | 7/2016 |

OTHER PUBLICATIONS

Wileman et al., Identification of the macrophage mannose receptor as a 175-kDa membrane protein. Proc Natl Acad Sci U S A, 1986. 83(8): p. 2501-5.

East et al., The mannose receptor family. Biochim Biophys Acta, 2002. 1572(2-3): p. 364-86.

Taylor, M.E. and K. Drickamer, Structural requirements for high affinity binding of complex ligands by the macrophage mannose receptor. J Biol Chem, 1993. 268(1): p. 399-404.

Roussel, M., et al., Mass cytometry deep phenotyping of human mononuclear phagocytes and myeloid-derived suppressor cells from human blood and bone marrow. J Leukoc Biol, 2017. 102(2): p. 437-447.

Tsunashima, H., et al., Accumulated myeloid-derived suppressor cells demonstrate distinct phenotypes and functions in two non-alcoholic steatohepatitis mouse models. Hepatobiliary Surg Nutr, 2015. 4(5): p. 313-9.

Engering, A.J., et al., The mannose receptor functions as a high capacity and broad specificity antigen receptor in human dendritic cells. Eur J Immunol, 1997. 27(9): p. 2417-25.7. Melief, J., et al., Phenotyping primary human microglia: tight regulation of LPS responsiveness. Glia, 2012. 60(10): p. 1506-17.

Maeda, H., et al., Polythiol-containing, recombinant mannosylated-albumin is a superior CD68+/CD206+ Kupffer cell-targeted nanoantioxidant for treatment of two acute hepatitis models. J Pharmacol Exp Ther, 2015. 352(2): p. 244-57.

Qin, Z., et al., Molecular Imaging of the Glomerulus via Mesangial Cell Uptake of Radiolabeled Tilmanocept. J Nucl Med, 2019.

Azad, A.K., et al., gamma-Tilmanocept, a New Radiopharmaceutical Tracer for Cancer Sentinel Lymph Nodes, Binds to the Mannose Receptor (CD206). J Immunol, 2015.

Surasi, D.S., J. O'Malley, and P. Bhambhvani, 99mTc-Tilmanocept: A Novel Molecular Agent for Lymphatic Mapping and Sentinel Lymph Node Localization. J Nucl Med Technol, 2015. 43(2): p. 87-91.

Chanmee, T., et al., Tumor-associated macrophages as major players in the tumor microenvironment. Cancers (Basel), 2014. 6(3): p. 1670-90.

Wallace, A.M., et al., Lymphoseek: a molecular radiopharmaceutical for sentinel node detection. Ann Surg Oncol, 2003. 10(5): p. 531-8.

Zanni, M.V., et al., Application of a Novel CD206+ Macrophage-Specific Arterial Imaging Strategy in HIV. J Infect Dis, 2017.

(Continued)

*Primary Examiner* — Sean M Basquill

(74) *Attorney, Agent, or Firm* — Fredrikson & Byron, P.A.

(57) ABSTRACT

Provided are compounds, compositions, methods, and kits for increasing target specificity of a mannosylated carbohydrate polymeric therapeutic or diagnostic compound to reduce or eliminate localization of the mannosylated carbohydrate polymeric therapeutic or diagnostic compound to off-target sites. Mannosylated carbohydrate polymers are synthesized to be modified to be either polyanionic (i.e., net negatively charged) or electrostatically neutral, and using these polyanionic or neutral mannosylated carbohydrate polymers as competitors for polycationic (i.e., net positively charged) mannosylated carbohydrate polymers carrying small molecule drug payloads or imaging moieties to CD206 expressing cells in target tissues, such as tumors or other sites of inflammation.

16 Claims, 2 Drawing Sheets

(56) References Cited

OTHER PUBLICATIONS

Hatami, E., et al., Mannose-decorated hybrid nanoparticles for enhanced macrophage targeting. Biochem Biophys Rep, 2019. 17: p. 197-207.
Kennedy, A., et al., Macrophages in synovial inflammation. Front Immunol, 2011. 2: p. 52.
Das, A., et al., High-Resolution Mapping and Dynamics of the Transcriptome, Transcription Factors, and Transcription Co-Factor Networks in Classically and Alternatively Activated Macrophages. Front Immunol, 2018. 9: p. 22.
Murray, P.J., et al., Macrophage activation and polarization: nomenclature and experimental guidelines. Immunity, 2014. 41(1): p. 14-20.
Smith, T.D., et al., Regulation of macrophage polarization and plasticity by complex activation signals. Integr Biol (Camb), 2016.
Dong, P., et al., CD86(+)/CD206(+), Diametrically Polarized Tumor-Associated Macrophages, Predict Hepatocellular Carcinoma Patient Prognosis. Int J Mol Sci, 2016. 17(3).
Kang, X.J., et al., Codelivery of dihydroartemisinin and doxorubicin in mannosylated liposomes for drug-resistant colon cancer therapy. Acta Pharmacol Sin, 2017. 38(6): p. 885-896.
Cope, F.O., et al., The inextricable axis of targeted diagnostic imaging and therapy: An immunological natural history approach. Nucl Med Biol, 2016. 43(3): p. 215-25.
Daldrup-Link, H. and L.M. Coussens, MR imaging of tumor-associated macrophages. Oncoimmunology, 2012. 1(4): p. 507-509.
Mehta, N.N., et al., Quantification of atherosclerotic plaque activity and vascular inflammation using [18-F] fluorodeoxyglucose positron emission tomography/computed tomography (FDG-PET/CT). J Vis Exp, 2012(63): p. e3777.
Gent, Y.Y., et al., Evaluation of the novel folate receptor ligand [18F]fluoro-PEG-folate for macrophage targeting in a rat model of arthritis. Arthritis Res Ther, 2013. 15(2): p. R37.
Tang, X., et al., Anti-tumour strategies aiming to target tumour-associated macrophages. Immunology, 2013. 138(2): p. 93-104.
Melief, J., et al., Phenotyping primary human microglia: tight regulation of LPS responsiveness. Glia, 2012. 60(10): p. 1506-17.
Zhang, M., et al., Plaque-hyaluronidase-responsive high-density-lipoprotein-mimetic nanoparticles for multistage intimal-macrophage-targeted drug delivery and enhanced anti-atherosclerotic therapy. Int J Nanomedicine, 2017. 12: p. 533-558.
Sun, X., et al., Molecular imaging of tumor-infiltrating macrophages in a preclinical mouse model of breast cancer. Theranostics, 2015. 5(6): p. 597-608.
Put, S., et al., SPECT imaging of joint inflammation with Nanobodies targeting the macrophage mannose receptor in a mouse model for rheumatoid arthritis. J Nucl Med, 2013. 54(5): p. 807-14.
Movahedi, K., et al., Nanobody-based targeting of the macrophage mannose receptor for effective in vivo imaging of tumor-associated macrophages. Cancer Res, 2012. 72(16): p. 4165-77.
Boschi et al. "Design and Synthesis of 99mTcN-Labeled Dextran-Mannose Derivatives for Sentinel Lymph Node Detection" Pharmaceuticals. Jul. 16, 2018, vol. 11, p. 1-15.
Bellato el al. "Mannosylaled Polycations Target CD206+ Antigen-Presenting Cells and Mediate T-Cell-Specific Activation in Cancer Vaccination" Biomacromolecules. Nov. 17, 2022, vol. 23, p. 5148-5163.
Nishikawa, M., et al., "Demonstration of the receptor-mediated hepatic uptake of dextran in mice." J Pharm Pharmacol, 1992. 44(5): p. 396-401.
Vera, D.R., et al., "A synthetic macromolecule for sentinel node detection: (99m)Tc-DTPA-mannosyl-dextran." J Nucl Med, 2001. 42(6): p. 951-9.
Takakura, Y., et al., "Disposition characteristics of macromolecules in tumor-bearing mice." Pharm Res, 1990. 7(4): p. 339-46.
Liu, S., et al., "Effect of variable domain charge on in vitro and in vivo disposition of monoclonal antibodies." MAbs, 2021. 13(1): p. 1993769.
Sun et al. "Enhancing Tumor Penetration of Nanomedicines" Biomacromolecules, May 8, 2017; 18(5): 1449-1459.
Jarad et al. "Update on the glomerular filtration barrier" Curr Opin Nephrol Hypertens, May 2009, 18(3): 226-232.
Brenner et al. "Glomeruler permselectivity: barrier function based on discrimination of molecular size and charge" The American Physiological Society, 1978, F455-.
Krasnici et al. "Effect of the Surface Charge of Liposomes on Their Uptake by Angiogenic Tumor Vessels" Int. J. Cancer, 2003, 105, 561-567.
Stylianopoulos et al. "Diffusion of Particles in the Extracellular Matrix: The Effect of Repulsive Electrostatic Interactions" Biophysical Journal, vol. 99, Sep. 2010, 1342-1349.
Stylianopoulos et al. "Cationic Nanoparticles Have Superior Transvascular Flux into Solid Tumors: Insights from a Mathematical Model" Ann Biomed Eng, Jan. 2013; 41(1).
Dellian et al. "Vascular permeability in a human tumour xenograft: molecular charge dependence" British Journal of Cancer, 2000, 82(9), 1513-1518.
Pustylnikov et al. "Targeting the C-type Lectins-Mediated Host-Pathogen Interactions with Dextran" J Pharm Pharm Sci, 2014, 17(3) 371-392.
Chou et al. "Investigation of the Spatiotemporal Responses of Nanoparticles in Tumor Tissues with a Small-Scale Mathematical Model" PLoS One, 2013, 8(4).
Claesson-Welsh, "Vascular permeability—the essentials" Upsala Journal of Medical Sciences, 2015, 120: 135-143.
Dreher et al. "Tumor Vascular Permeability, Accumulation, and Penetration of Macromolecular Drug Carriers" Journal of the National Cancer Institute, Mar. 1, 2006, vol. 98, No. 5.
Li et al. "Characterization of tumor vascular permeability using natural dextrans and CEST MRI" Magn Reson Med, Feb. 2018; 79(2): 1001-1009.
Hiroshi Maeda, "Vascular permeability in cancer and infection as related to macromolecular drug delivery, with emphasis on the EPR effect for tumor-selective drug targeting" Proc. Jpn. Acad., 2012, Ser. B 88, p. 53-71.
Movahedi et al. "Nanobody-Based Targeting of the Macrophage Mannose Receptor for Effective In Vivo Imaging of Tumor-Associated Macrophages" American Association for Cancer Research, Aug. 15, 2012, 72(16), p. 4165-4177.

* cited by examiner 3 4 5

Mannose Dextran

Sulfonate Dextran 6

ALTERING NET CHARGE ON MANNOSYLATED DEXTRANS TO MAXIMIZE TARGET TISSUE UPTAKE AND OFF TARGET COMPETITIVE BLOCKING

CROSS-REFERENCE TO RELATED APPLICATIONS

This application claims the benefit of U.S. Provisional Application Ser. No. 63/306,719, filed on Feb. 4, 2022 and entitled "Altering Net Charge on Mannosylated Dextrans to Maximize Target Tissue Uptake and Off Target Competitive Blocking," the entire contents of which are incorporated herein by reference.

TECHNICAL FIELD

The disclosure relates to chemical compounds, compositions, methods for reducing and eliminating off-target localization of mannosylated carbohydrate polymers by altering the net charge on the mannosylated carbohydrate polymers and/or co-administering a mannosylated carbohydrate polymer with a charged compound to maximize target tissue uptake and off-target competitive blocking.

BACKGROUND

Macrophages are significant contributors to the pathobiology of many societally significant illnesses. In lesions of macrophage involved illnesses, macrophages may aggregate in large numbers at sites of injury, infection, or in many autoimmune diseases. In an aspect, examples of macrophage involved illnesses include but are not limited to cancer, atherosclerosis, rheumatoid arthritis, other autoimmune diseases. Macrophages respond to various stimuli in their local microenvironment by altering their expression patterns for many genes, potentially hundreds. Such phenotypically altered macrophages are said to be activated macrophages. Depending upon to which stimuli a macrophage is responding, a wide range of activated phenotypic states can be attained. Among those genes that can be differentially expressed upon macrophage activation is the macrophage mannose receptor, CD206, which is highly up regulated in a large proportion of activated macrophages residing at sites of inflammation, such as but not limited to, tumors (i.e. tumor associated macrophages—TAMs), atherosclerosis, and rheumatoid arthritis.

Because macrophages are both abundant in the lesions of macrophage involved illnesses and contribute significantly to the pathobiology of these diseases, many investigators have targeted imaging agents to macrophages as a tool to diagnose these conditions and/or have targeted therapeutics to macrophages as a strategy to treat macrophage involved conditions. Also, because CD206 is typically highly expressed on activated macrophages residing in lesions of macrophage involved illnesses, many investigators have evaluated CD206 targeted agents to either image and/or treat these lesions or illnesses.

CD206 is a transmembrane C-type lectin with high affinity for binding ligands displaying multiple terminal moieties of the sugar, mannose. CD206 is expressed on various cell types of the myeloid lineage including macrophages (including tissue resident macrophages), myeloid derived suppressor cells (MDSC), dendritic cells, and mesangial cells of the kidney.

Importantly, CD206 is expressed by Kupffer cells. Kupffer cells are resident macrophage-like cells of the liver that occur in large numbers along the walls of sinusoid capillaries. Thus, Kupffer cells are in direct contact with the blood. Another important class of CD206 expressing cell is comprised of the mesangial cells, which reside in the glomeruli of the kidneys. Mesangial cells are an unusual cell type with characteristics of both macrophages and smooth muscle. Mesangial cells are separated from the blood by a porous glomerular membrane and an incomplete layer of endothelial cells with gaps between the cells, thus affording mesangial cells largely unobstructed interaction with macromolecules in the blood that are small enough to pass through the globular membrane. The spleen contains a large number of macrophages that the immune system holds in reserve to be mobilized to sites of injury or infection when such injury or infection events occur. There are minimal barriers between the blood flow and macrophages in the spleen.

Nearly all other macrophages reside in tissues with intact capillary blood flow. The intact capillary wall is a significant barrier through which macromolecules must pass in order to gain access to tissues. Thus, macrophages residing in tissues with intact capillaries do not have direct contact with the blood. Tissues are comprised of cells and extracellular matrix (EM). As such, cells and EM also constitute a significant barrier through which macromolecules must pass or diffuse in order to gain access to tissue cells, including most tissue resident macrophages. However, at sites of pathological lesions with chronic inflammation, incompletely or poorly formed capillaries are commonly observed with incomplete endothelial cells layers separating the lumen of capillaries from the surrounding tissues. Such capillaries are said to be leaky and are less efficient at excluding macromolecules and other relatively large structures such as nanoparticles or liposomes from exiting the blood and entering the surrounding tissues. Examples of pathological lesions with chronic inflammation in which leaky capillaries have been observed include, but are not limited to, inflamed joints in patients with rheumatoid arthritis, atherosclerotic plaques in the walls of arteries, and cancerous tumors. However, once macromolecules, nanoparticles, or liposomes have entered a pathological lesion after passing through the wall of a leaky capillary, their further diffusion into the surrounding tissues continues to be impeded by cells and EM.

Tilmanocept is a synthetic molecular construct created by attaching mannose moieties and the chelating agent, diethylenetriamine pentaacetic acid (DTPA) to a 10 kD dextran backbone via amine terminated leashes. Tilmanocept has an average of 17 mannose moieties, 5 DTPA moieties, and various numbers of unoccupied amine terminated leashes per dextran backbone molecule. Tilmanocept is a member of a class of related constructs referred to as mannosylated dextrans. Mannosylated dextrans can be constructed using dextrans of varying sizes with varying numbers of mannose moieties attached to the dextran backbone by molecular leashes of varying compositions. To these constructs, numerous types of other moieties, DTPA being but one example, may be conjugated. Mannosylated dextrans generally and tilmanocept specifically are intentionally designed to be high affinity ligands for certain C-type lectins and especially for the macrophage mannose receptor, CD206. When injected into the blood, mannosylated dextrans have relatively short blood half-lives. In humans, the blood half-life of tilmanocept has been observed to be about 20 minutes.

Mannosylated dextrans are being developed as drug delivery vehicles for delivery of small molecule payloads and imaging agents targeted to TAMs and other sites of inflammation, where CD206 expressing macrophages are abundant. Examples include U.S. patent application Ser. Nos. 16/041,673; 16/832,620; 16/773,512; and Ser. No. 16/997,648, all of which are hereby incorporated by reference in their entirety. However, off-target localization, especially through binding to CD206 expressing cells in the liver (i.e., Kupffer cells), the kidney (i.e., mesangial cells), and spleen have undesirable and/or dose limiting consequences. One solution for addressing the off-target localization issue was described within U.S. patent application Ser. No. 17/039,409, which is hereby incorporated by reference in its entirety. This solution involved the development of two mannosylated amine dextrans (MAD constructs) with differing molecular weights (i.e., size). In an aspect, the efficiency by which macromolecules, including MAD constructs, penetrate into tissues from the blood flow (i.e., pass through the capillary wall and diffuse through the EM) is inversely proportional to their sizes (i.e., molecular weights). As a result, small molecules penetrate into tissues more efficiently than larger molecules. However, these barriers do not exist for Kupffer cells (which are directly exposed to blood flow) and are highly minimized for splenic macrophages and mesangial cells. As such, the reference is directed to the administration of a low molecular weight MAD carrying a payload of either an imaging and/or a therapeutic moiety to an animal or human subject, and further administering an excess of a high molecular weight MAD (HMW-MAD) without a payload. In some aspects, the HMW-MAD without payload is provided in molar excess of the low-molecular weight MAD in a range of 1.5-fold to 10-fold. The HMW-MAD thus binds to CD206 on Kupffer cells, competing with the small molecular weight MAD carrying the payload for CD206 binding sites. Due to its large size, the HMW-MAD is restricted from entering tumors (or other target tissues) and cannot compete with the payload carrying small molecular weight MAD for CD206 binding sites on TAMs. The small molecular weight MAD efficiently enters the tumor and binds to CD206 without HMW-MAD competition. Thus, off-target binding of a MAD construct with a payload to the Kupffer cells of the liver was reduced by 50% or more without decreasing localization to TAMs in tumors.

However, due to the large molecular weight (i.e. size) of the HMW-MAD, current solutions do not efficiently block localization of a MAD carrying a payload to the spleen or mesangial cells of the kidney. Therefore, there is an ongoing need for additional solutions to block off-target localization to areas containing certain C-type lectins and especially for the macrophage mannose receptor, CD206.

Accordingly, there is a need in the art for alternative means to synthesize carbohydrate polymer constructs with differential localization potential to avoid off-target liver, spleen, and mesangial cell localization while promoting equal or greater localization to target tissues, such as tumors (TAMs, dendritic cells, and MDSC), and/or to sites of inflammation or infection.

SUMMARY

Disclosed herein are compounds, compositions, methods, and kits for increasing target specificity of a mannosylated carbohydrate polymeric therapeutic or diagnostic compound to reduce or eliminate localization of the mannosylated carbohydrate polymeric therapeutic or diagnostic compound to off-target sites.

In Example 1, a method of increasing target specificity of a mannosylated carbohydrate polymeric therapeutic or diagnostic compound in a subject comprises, administering a blocking compound, and administering an effective amount of the mannosylated carbohydrate polymeric therapeutic or diagnostic compound comprising a carbohydrate polymer backbone and one or more CD206 targeting moieties and one or more therapeutic or diagnostic agents attached thereto, wherein the blocking compound is polyanionic and thereby negatively charged, or neutral, and wherein the mannosylated carbohydrate polymeric therapeutic or diagnostic compound is polycationic and thereby positively charged.

Example 2 relates to the method according to Example 1, wherein the method reduces or eliminates localization of the mannosylated carbohydrate polymeric therapeutic or diagnostic compound to off-target sites comprising the liver, the kidney, and/or the spleen of the subject.

Example 3 relates to the method according to Example 1 or 2, wherein the mannosylated carbohydrate polymeric therapeutic or diagnostic compound is a compound of Formula (I):

(I)

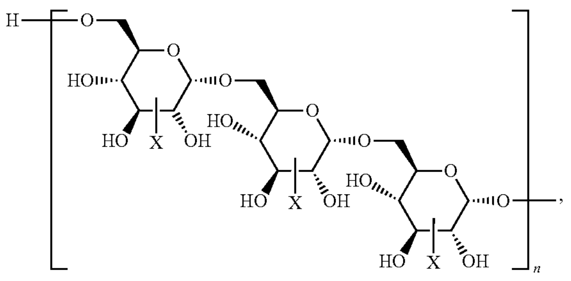

wherein

- each X is independently H, L1-A, L2-R, L3-W, or L4-A-W;
- each L1, L2, L3, and L4 are independently leashes;
- each A independently comprises a therapeutic agent, a diagnostic agent, or H;
- each R independently comprises a mannose-binding C-type lectin receptor targeting moiety or H;
- each W is independently a terminal amine group comprising a linear or branched polyamine, guanidine, or quaternary ammonium moiety; and
- n is an integer greater than zero, wherein each unit of n may be the same or different; and
- wherein at least one R comprises a mannose-binding C-type lectin receptor targeting moiety selected from the group consisting of mannose, galactose, fucose, N-acetylgalactosamine (GalNAc), N-acetylglucosamine (GlcNAc), and/or glucuronic acid, and at least one A comprises a therapeutic agent or diagnostic agent.

Example 4 relates to the method according to Example 3, wherein each of L1 and L2 comprises the formula $-(CH_2)_pS(CH_2)_q-NH-$, wherein p and q are integers from 0 to 5, and wherein each L3 comprises the formula $-(CH_2)_pS(CH_2)_q-$, wherein p and q are integers from 0 to 5.

Example 5 relates to the method according to any one of Examples 1 to 4, wherein the blocking compound is a compound of Formula (II):

(II)

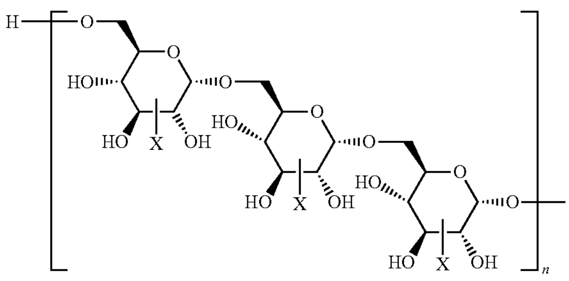

wherein each X is H, L1-R, or L2-Y;

each L1 and L2 are independently leashes;

each R independently comprises a mannose-binding C-type lectin receptor targeting moiety or H;

each Y independently comprises a carboxylate, sulfate, sulfonate, sulfinate, phosphate, phosphonate, phosphinate, or mannose moiety, or H; and n is an integer greater than zero, wherein each unit of n may be the same or different; and wherein at least one R comprises a mannose-binding C-type lectin receptor targeting moiety selected from the group consisting of mannose, galactose, fucose, N-acetylgalactosamine (GalNAc), N-acetylglucosamine (GlcNAc), and/or glucuronic acid; and wherein at least one Y comprises a carboxylate, sulfate, sulfonate, sulfinate, phosphate, phosphonate, phosphinate, or mannose moiety.

Example 6 relates to the method according to Example 5, wherein when at least one Y is the mannose moiety, each Y within formula (II) must be the mannose moiety.

Example 7 relates to the method according to any one of Examples 1 to 6, wherein the blocking compound does not contain a therapeutic or diagnostic agent.

Example 8 relates to the method according to any one of Examples 1 to 7, wherein the blocking compound backbone has a molecular weight of from about 1 kDa to about 500 kDa, and the mannosylated carbohydrate polymeric therapeutic or diagnostic compound dextran backbone has a molecular weight of from about 1 kDa to about 20 kDa.

Example 9 relates to the method according to any one of Examples 1 to 8, wherein the step of administering the blocking compound is followed by a time interval of 0 to about 60 minutes before the step of administering the mannosylated carbohydrate polymeric therapeutic or diagnostic compound.

Example 10 relates to the method according to any one of Examples 1 to 8, wherein the blocking compound and the mannosylated carbohydrate polymeric therapeutic or diagnostic compound are administered simultaneously.

Example 11 relates to the method according to any one of Examples 1 to 10, wherein the mannosylated carbohydrate polymeric therapeutic or diagnostic compound comprises the one or more therapeutic agents.

Example 12 relates to the method according to any one of Examples 1 to 11, wherein the portion of the administered dose of the mannosylated carbohydrate polymeric therapeutic or diagnostic compound that localizes to a desired target tissue other than the liver, kidney, and/or spleen is higher than the localizing portion of the mannosylated carbohydrate polymeric therapeutic or diagnostic compound without administration of the blocking compound.

Example 13 relates to the method according to any one of Examples 1 to 12, wherein the effective dose of the mannosylated carbohydrate polymeric therapeutic or diagnostic compound is lower than the effective does of the mannosylated carbohydrate polymeric therapeutic or diagnostic compound without administration of the blocking compound.

Example 14 relates to the method according to any one of Examples 1 to 13, wherein the blocking compound preferentially binds to CD206 expressing cells in the liver, kidney, and/or spleen.

Example 15 relates to the method according to any one of Examples 1 to 14, wherein the mannosylated carbohydrate polymeric therapeutic or diagnostic compound has decreased binding to CD206 cells in the liver, kidney, and/or spleen relative to a subject administered a comparable dose of mannosylated carbohydrate polymeric therapeutic or diagnostic compound without administration of the blocking compound.

Example 16 relates to the method according to any one of Examples 1 to 15, wherein the subject has been diagnosed with an autoimmune disease, an inflammatory disease, or cancer.

In Example 17, a blocking compound comprises the compound of Formula (II):

(II)

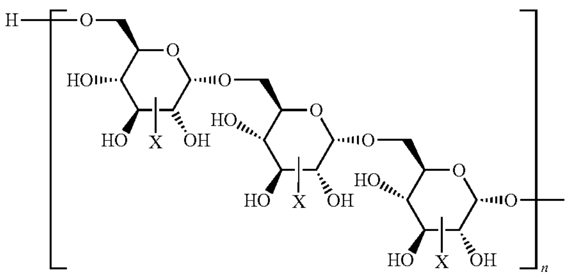

wherein each X is H, L1-R, or L2-Y;

each L1 and L2 are independently leashes;

each R independently comprises a mannose-binding C-type lectin receptor targeting moiety or H;

each Y independently comprises a carboxylate, sulfate, sulfonate, sulfinate, phosphate, phosphonate, phosphinate, or mannose moiety, or H; and n is an integer greater than zero, wherein each unit of n may be the same or different; and wherein at least one R comprises a mannose-binding C-type lectin receptor targeting moiety selected from the group consisting of mannose, galactose, fucose, N-acetylgalactosamine (GalNAc), N-acetylglucosamine (GlcNAc), and/or glucuronic acid; and wherein at least one Y comprises a carboxylate, sulfate, sulfonate, sulfinate, phosphate, phosphonate, phosphinate, or mannose moiety.

Example 18 relates to the compound according to Example 17, wherein the blocking compound does not contain a therapeutic or diagnostic agent.

Example 19 relates to the compound according to Example 17 or 18, wherein the blocking compound backbone has a molecular weight of from about 1 kDa to about 500 kDa.

Example 20 relates to the compound according to any one of Examples 17 to 19, wherein when at least one Y is the mannose moiety, each Y within formula (II) must be the mannose moiety.

Example 21 relates to the compound according to any one of Examples 17 to 19, wherein at least one Y is a carboxylate or sulfonate moiety.

Example 22 relates to the compound according to any one of Examples 17 to 21, wherein each of L1 and L2 independently comprise the formula $-(CH_2)_pS(CH_2)_q-NH-$, wherein p and q are integers from 0 to 5.

In Example 23, a composition comprises a blocking compound, and a mannosylated carbohydrate polymeric therapeutic or diagnostic compound comprising a dextran backbone and one or more CD206 targeting moieties and one or more therapeutic agents attached thereto, wherein the blocking compound is polyanionic and thereby negatively charged, or neutral, and wherein the mannosylated carbohydrate polymeric therapeutic or diagnostic compound is polycationic and thereby positively charged.

Example 24 relates to the composition according to Example 23, wherein the blocking compound comprises the compound of Formula (II):

(II)

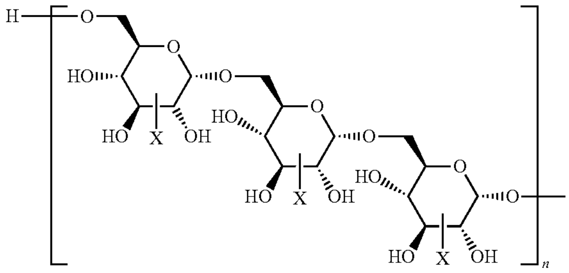

wherein each X is H, L1-R, or L2-Y;

each L1 and L2 are independently leashes;

each R independently comprises a mannose-binding C-type lectin receptor targeting moiety or H;

each Y independently comprises a carboxylate, sulfate, sulfonate, sulfinate, phosphate, phosphonate, phosphinate, or mannose moiety, or H; and n is an integer greater than zero, wherein each unit of n may be the same or different; and wherein at least one R comprises a mannose-binding C-type lectin receptor targeting moiety selected from the group consisting of mannose, galactose, fucose, N-acetylgalactosamine (GalNAc), N-acetylglucosamine (GlcNAc), and/or glucuronic acid; and wherein at least one Y comprises a carboxylate, sulfate, sulfonate, sulfinate, phosphate, phosphonate, phosphinate, or mannose moiety.

Example 25 relates to the composition according to Example 24, wherein at least one Y is a carboxylate or sulfonate moiety.

Example 26 relates to the composition according to any one of Examples 23 to 25, wherein the mannosylated carbohydrate polymeric therapeutic or diagnostic compound is a compound of Formula (I):

(I)

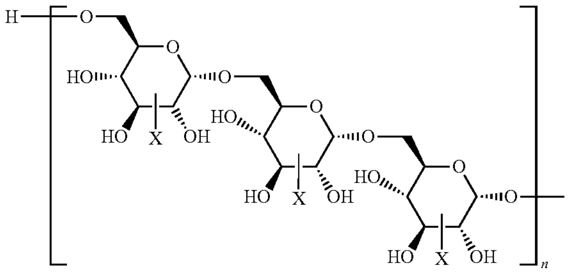

wherein each X is independently H, L1-A, L2-R, L3-W, or L4-A-W;

each L1, L2, L3, and L4 are independently leashes;

each A independently comprises a therapeutic agent, a diagnostic agent, or H;

each R independently comprises a mannose-binding C-type lectin receptor targeting moiety or H;

each W is independently a terminal amine group comprising a linear or branched polyamine, guanidine, or quaternary ammonium moiety; and n is an integer greater than zero, wherein each unit of n may be the same or different; and wherein at least one R comprises a mannose-binding C-type lectin receptor targeting moiety selected from the group consisting of mannose, galactose, fucose, N-acetylgalactosamine (GalNAc), N-acetylglucosamine (GlcNAc), and/or glucuronic acid, and at least one A comprises a therapeutic agent or diagnostic agent.

Example 27 is related to the composition according to any one of Examples 23 to 26, wherein the blocking compound backbone has a molecular weight of from about 1 kDa to about 500 kDa, and the mannosylated carbohydrate polymeric therapeutic or diagnostic compound dextran backbone has a molecular weight of from about 1 kDa to about 20 kDa.

While multiple embodiments are disclosed, still other embodiments of the present invention will become apparent to those skilled in the art from the following detailed description, which shows and describes illustrative embodiments of the invention. As will be realized, the disclosure is capable of modifications in various obvious aspects, all without departing from the spirit and scope of the disclosure. Accordingly, the figures, if present, and detailed description are to be regarded as illustrative in nature and not restrictive.

DETAILED DESCRIPTION

Figure 1A:
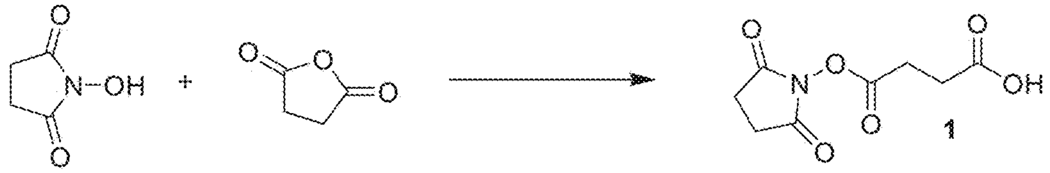
FIG. 1A shows a reaction scheme in preparing NHS ester 1 with succinic anhydride.

It is to be understood that all terminology used herein is for the purpose of describing particular embodiments only and is not intended to be limiting in any manner or scope.

For example, as used in this specification and the appended claims, the singular forms "a," "an" and "the" can include plural referents unless the content clearly indicates otherwise. Further, all units, prefixes, and symbols may be denoted in its SI accepted form.

Numeric ranges recited within the specification are inclusive of the numbers defining the range and include each integer within the defined range. Throughout this disclosure, various aspects of this invention are presented in a range format. It should be understood that the description in range format is merely for convenience and brevity and should not be construed as an inflexible limitation on the scope of the invention. Accordingly, the description of a range should be considered to have specifically disclosed all the possible sub-ranges, fractions, and individual numerical values within that range. For example, description of a range such as from 1 to 6 should be considered to have specifically disclosed sub-ranges such as from 1 to 3, from 1 to 4, from 1 to 5, from 2 to 4, from 2 to 6, from 3 to 6 etc., as well as individual numbers within that range, for example, 1, 2, 3, 4, 5, and 6, and decimals and fractions, for example, 1.2, 3.8, 1½, and 4¾ This applies regardless of the breadth of the range.

Ranges can be expressed herein as from "about" one particular value, and/or to "about" another particular value. When such a range is expressed, a further aspect includes from the one particular value and/or to the other particular value. Similarly, when values are expressed as approximations, by use of the antecedent "about," it will be understood that the particular value forms a further aspect. It will be further understood that the endpoints of each of the ranges are significant both in relation to the other endpoint, and independently of the other endpoint. It is also understood that there are a number of values disclosed herein, and that each value is also herein disclosed as "about" that particular value in addition to the value itself. For example, if the value "10" is disclosed, then "about 10" is also disclosed. It is also understood that each unit between two particular units are also disclosed. For example, if 10 and 15 are disclosed, then 11, 12, 13, and 14 are also disclosed.

As used herein, the term "substantially free" refers to compositions completely lacking the component or having such a small amount of the component that the component does not affect the performance of the composition. The component may be present as an impurity or as a contaminant and shall be less than 0.5 wt-%. In another embodiment, the amount of the component is less than 0.1 wt-% and in yet another embodiment, the amount of component is less than 0.01 wt-%.

The term "weight percent," "wt-%," "percent by weight," "% by weight," and variations thereof, as used herein, refer to the concentration of a substance as the weight of that substance divided by the total weight of the composition and multiplied by 100. It is understood that, as used here, "percent," "%," and the like are intended to be synonymous with "weight percent," "wt-%," etc.

The compounds, compositions, methods, kits, and systems of the present invention may comprise, consist essentially of, or consist of the components and ingredients of the present invention as well as other ingredients described herein. As used herein, "consisting essentially of" means that the compounds, compositions, methods, kits, and systems may include additional steps, components or ingredients, but only if the additional steps, components or ingredients do not materially alter the basic and novel characteristics of the claimed compounds, compositions, methods, kits, and systems.

A residue of a chemical species, as used in the specification and concluding claims, refers to the moiety that is the resulting product of the chemical species in a particular reaction scheme or subsequent formulation or chemical product, regardless of whether the moiety is actually obtained from the chemical species. Thus, an ethylene glycol residue in a polyester refers to one or more —OCH2CH2O— units in the polyester, regardless of whether ethylene glycol was used to prepare the polyester. Similarly, a sebacic acid residue in a polyester refers to one or more $—CO(CH_2)_8CO—$ moieties in the polyester, regardless of whether the residue is obtained by reacting sebacic acid or an ester thereof to obtain the polyester.

As used herein, the term "substituted" is contemplated to include all permissible substituents of organic compounds. In a broad aspect, the permissible substituents include acyclic and cyclic, branched and unbranched, carbocyclic and heterocyclic, and aromatic and nonaromatic substituents of organic compounds. Illustrative substituents include, for example, those described below. The permissible substituents can be one or more and the same or different for appropriate organic compounds. For purposes of this disclosure, the heteroatoms, such as nitrogen, can have hydrogen substituents and/or any permissible substituents of organic compounds described herein which satisfy the valences of the heteroatoms. This disclosure is not intended to be limited in any manner by the permissible substituents of organic compounds. Also, the terms "substitution" or "substituted with" include the implicit proviso that such substitution is in accordance with permitted valence of the substituted atom and the substituent, and that the substitution results in a stable compound, e.g., a compound that does not spontaneously undergo transformation such as by rearrangement, cyclization, elimination, etc. It is also contemplated that, in certain aspects, unless expressly indicated to the contrary, individual substituents can be further optionally substituted (i.e., further substituted or unsubstituted).

In defining various terms, "A1," "A2," "A3," and "A4" are used herein as generic symbols to represent various specific substituents. These symbols can be any substituent, not limited to those disclosed herein, and when they are defined to be certain substituents in one instance, they can, in another instance, be defined as some other substituents.

"R1," "R2," "R3," "Rn," where n is an integer, as used herein can, independently, possess one or more of the groups listed above. For example, if R1 is a straight chain alkyl group, one of the hydrogen atoms of the alkyl group can optionally be substituted with a hydroxyl group, an alkoxy group, an alkyl group, a halide, and the like. Depending upon the groups that are selected, a first group can be incorporated within second group or, alternatively, the first group can be pendant (i.e., attached) to the second group. For example, with the phrase "an alkyl group comprising an amino group," the amino group can be incorporated within the backbone of the alkyl group. Alternatively, the amino group can be attached to the backbone of the alkyl group. The nature of the group(s) that is (are) selected will determine if the first group is embedded or attached to the second group.

As described herein, compounds of the invention may contain "optionally substituted" moieties. In general, the term "substituted," whether preceded by the term "optionally" or not, means that one or more hydrogens of the designated moiety are replaced with a suitable substituent. Unless otherwise indicated, an "optionally substituted" group may have a suitable substituent at each substitutable position of the group, and when more than one position in any given structure may be substituted with more than one substituent selected from a specified group, the substituent may be either the same or different at every position. Combinations of substituents envisioned by this invention are preferably those that result in the formation of stable or chemically feasible compounds. In is also contemplated that, in certain aspects, unless expressly indicated to the contrary, individual substituents can be further optionally substituted (i.e., further substituted or unsubstituted).

Certain materials, compounds, compositions, and components disclosed herein can be obtained commercially or readily synthesized using techniques generally known to those of skill in the art. For example, the starting materials and reagents used in preparing the disclosed compounds and compositions are either available from commercial suppliers such as Aldrich Chemical Co., (Milwaukee, Wis.), Acros Organics (Morris Plains, N.J.), Fisher Scientific (Pittsburgh, Pa.), or Sigma (St. Louis, Mo.) or are prepared by methods known to those skilled in the art following procedures set forth in references such as Fieser and Fieser's Reagents for Organic Synthesis, Volumes 1-17 (John Wiley and Sons, 1991); Rodd's Chemistry of Carbon Compounds, Volumes 1-5 and Supplementals (Elsevier Science Publishers, 1989); Organic Reactions, Volumes 1-40 (John Wiley and Sons, 1991); March's Advanced Organic Chemistry, (John Wiley and Sons, 4th Edition); and Larock's Comprehensive Organic Transformations (VCH Publishers Inc., 1989).

Disclosed are the components to be used to prepare the compositions of the invention as well as the compositions themselves to be used within the methods disclosed herein. These and other materials are disclosed herein, and it is understood that when combinations, subsets, interactions, groups, etc. of these materials are disclosed that while specific reference of each various individual and collective combinations and permutation of these compounds cannot be explicitly disclosed, each is specifically contemplated and described herein. For example, if a particular compound is disclosed and discussed and a number of modifications that can be made to a number of molecules including the compounds are discussed, specifically contemplated is each and every combination and permutation of the compound and the modifications that are possible unless specifically indicated to the contrary. Thus, if a class of molecules A, B, and C are disclosed as well as a class of molecules D, E, and F and an example of a combination molecule, A-D is disclosed, then even if each is not individually recited each is individually and collectively contemplated meaning combinations, A-E, A-F, B-D, B-E, B-F, C-D, C-E, and C-F are considered disclosed. Likewise, any subset or combination of these is also disclosed. Thus, for example, the sub-group of A-E, B-F, and C-E would be considered disclosed. This concept applies to all aspects of this application including, but not limited to, steps in methods of making and using the compositions of the invention. Thus, if there are a variety of additional steps that can be performed it is understood that each of these additional steps can be performed with any specific embodiment or combination of embodiments of the methods of the invention.

As used herein, the term "pharmaceutically acceptable carrier" or "carrier" refers to sterile aqueous or nonaqueous solutions, colloids, dispersions, suspensions or emulsions, as well as sterile powders for reconstitution into sterile injectable solutions or dispersions just prior to use. Examples of suitable aqueous and nonaqueous carriers, diluents, solvents or vehicles include water, ethanol, polyols (such as glycerol, propylene glycol, polyethylene glycol and the like), carboxymethylcellulose and suitable mixtures thereof, vegetable oils (such as olive oil) and injectable organic esters such as ethyl oleate. Proper fluidity can be maintained, for example, by the use of coating materials such as lecithin, by the maintenance of the required particle size in the case of dispersions and by the use of surfactants. These compositions can also contain adjuvants such as preservatives, wetting agents, emulsifying agents and dispersing agents. Prevention of the action of microorganisms can be ensured by the inclusion of various antibacterial and antifungal agents such as paraben, chlorobutanol, phenol, sorbic acid and the like. It can also be desirable to include isotonic agents such as sugars, sodium chloride and the like. Prolonged absorption of the injectable pharmaceutical form can be brought about by the inclusion of agents, such as aluminum monostearate and gelatin, which delay absorption. Injectable depot forms are made by forming microencapsule matrices of the drug in biodegradable polymers such as polylactide-polyglycolide, poly(orthoesters) and poly(anhydrides). Depending upon the ratio of drug to polymer and the nature of the particular polymer employed, the rate of drug release can be controlled. Depot injectable formulations are also prepared by entrapping the drug in liposomes or microemulsions which are compatible with body tissues. The injectable formulations can be sterilized, for example, by filtration through a bacterial-retaining filter or by incorporating sterilizing agents in the form of sterile solid compositions which can be dissolved or dispersed in sterile water or other sterile injectable media just prior to use. Suitable inert carriers can include sugars such as lactose. Desirably, at least 95% by weight of the particles of the active ingredient have an effective particle size in the range of 0.01 to 10 micrometers.

As used herein, the term "cancer" refers to cells having the capacity for autonomous growth. Examples of such cells include cells having an abnormal state or condition characterized by rapidly proliferating cell growth. The term is meant to include cancerous growths, e.g., tumors; oncogenic processes, metastatic tissues, and malignantly transformed cells, tissues, or organs, irrespective of histopathologic type or stage of invasiveness. Also included are malignancies of the various organ systems, such as respiratory, cardiovascular, renal, reproductive, hematological, neurological, hepatic, gastrointestinal, and endocrine systems; as well as adenocarcinomas which include malignancies such as most colon cancers, renal-cell carcinoma, prostate cancer and/or testicular tumors, non-small cell carcinoma of the lung, cancer of the small intestine, and cancer of the esophagus. Cancer that is "naturally arising" includes any cancer that is not experimentally induced by implantation of cancer cells into a subject, and includes, for example, spontaneously arising cancer, cancer caused by exposure of a patient to a carcinogen(s), cancer resulting from insertion of a transgenic oncogene or knockout of a tumor suppressor gene, and cancer caused by infections, e.g., viral infections. The term "carcinoma" is art recognized and refers to malignancies of epithelial or endocrine tissues. In some embodiments, the present methods can be used to treat a subject having an epithelial cancer, e.g., a solid tumor of epithelial origin, e.g., lung, breast, ovarian, prostate, renal, pancreatic, or colon cancer.

As used herein, the term "subject" refers to the target of administration, e.g., an animal. Thus, the subject of the herein disclosed methods can be a vertebrate, such as a mammal, a fish, a bird, a reptile, or an amphibian. Alternatively, the subject of the herein disclosed methods can be a human, non-human primate, horse, pig, rabbit, dog, sheep, goat, cow, cat, guinea pig or rodent. The term does not denote a particular age or sex. Thus, adult and newborn subjects, as well as fetuses, whether male or female, are intended to be covered. In one aspect, the subject is a mammal. A patient refers to a subject afflicted with a disease or disorder. The term "patient" includes human and veterinary subjects. In some aspects of the disclosed methods, the subject has been diagnosed with a need for treatment of one or more cancer disorders prior to the administering step.

As used herein, the term "treatment" refers to the medical management of a patient with the intent to cure, ameliorate, stabilize, or prevent a disease, pathological condition, or disorder. This term includes active treatment, that is, treatment directed specifically toward the improvement of a disease, pathological condition, or disorder, and also includes causal treatment, that is, treatment directed toward removal of the cause of the associated disease, pathological condition, or disorder. In addition, this term includes palliative treatment, that is, treatment designed for the relief of symptoms rather than the curing of the disease, pathological condition, or disorder; preventative treatment, that is, treatment directed to minimizing or partially or completely inhibiting the development of the associated disease, pathological condition, or disorder; and supportive treatment, that is, treatment employed to supplement another specific therapy directed toward the improvement of the associated disease, pathological condition, or disorder. In various aspects, the term covers any treatment of a subject, including a mammal (e.g., a human), and includes: (i) preventing the disease from occurring in a subject that can be predisposed to the disease but has not yet been diagnosed as having it; (ii) inhibiting the disease, i.e., arresting its development; or (iii) relieving the disease, i.e., causing regression of the disease. In one aspect, the subject is a mammal such as a primate, and, in a further aspect, the subject is a human. The term "subject" also includes domesticated animals (e.g., cats, dogs, etc.), livestock (e.g., cattle, horses, pigs, sheep, goats, etc.), and laboratory animals (e.g., mouse, rabbit, rat, guinea pig, fruit fly, etc.).

As used herein, the term "prevent" or "preventing" refers to precluding, averting, obviating, forestalling, stopping, or hindering something from happening, especially by advance action. It is understood that where reduce, inhibit or prevent are used herein, unless specifically indicated otherwise, the use of the other two words is also expressly disclosed.

As used herein, the term "diagnosed" means having been subjected to a physical examination by a person of skill, for example, a physician, and found to have a condition that can be diagnosed or treated by the compounds, compositions, or methods disclosed herein. For example, "diagnosed with cancer" means having been subjected to a physical examination by a person of skill, for example, a physician, and found to have a condition that can be diagnosed or treated by a compound or composition that can reduce tumor size or slow rate of tumor growth. A subject having cancer, tumor, or at least one cancer or tumor cell, may be identified using methods known in the art. For example, the anatomical position, gross size, and/or cellular composition of cancer cells or a tumor may be determined using contrast-enhanced MRI or CT. Additional methods for identifying cancer cells can include, but are not limited to, ultrasound, bone scan, surgical biopsy, and biological markers (e.g., serum protein levels and gene expression profiles). An imaging solution comprising a cell-sensitizing composition of the present invention may be used in combination with MRI or CT, for example, to identify cancer cells.

As used herein, the terms "administering" and "administration" refer to any method of providing a pharmaceutical preparation to a subject. Such methods are well known to those skilled in the art and include, but are not limited to, oral administration, transdermal administration, administration by inhalation, nasal administration, topical administration, intravaginal administration, ophthalmic administration, intraaural administration, intracerebral administration, rectal administration, sublingual administration, buccal administration, and parenteral administration, including injectable such as intravenous administration, intra-arterial administration, administration to specific organs through invasion, intramuscular administration, intratumoral administration, and subcutaneous administration. Administration can be continuous or intermittent. In various aspects, a preparation can be administered therapeutically; that is, administered to treat an existing disease or condition. In further various aspects, a preparation can be administered prophylactically; that is, administered for prevention of a disease or condition.

As used herein, the terms "effective amount" and "amount effective" refer to an amount that is sufficient to achieve the desired result or to have an effect on an undesired condition. For example, a "therapeutically effective amount" refers to an amount that is sufficient to achieve the desired therapeutic result or to have an effect on undesired symptoms but is generally insufficient to cause adverse side effects. The specific therapeutically effective dose level for any particular patient will depend upon a variety of factors including the disorder being treated and the severity of the disorder; the specific composition employed; the age, body weight, general health, sex and diet of the patient; the time of administration; the route of administration; the rate of excretion of the specific compound employed; the duration of the treatment; drugs used in combination or coincidental with the specific compound employed and like factors well known in the medical arts. For example, it is well within the skill of the art to start doses of a compound at levels lower than those required to achieve the desired therapeutic effect and to gradually increase the dosage until the desired effect is achieved. If desired, the effective daily dose can be divided into multiple doses for purposes of administration. Consequently, single dose compositions can contain such amounts or submultiples thereof to make up the daily dose. The dosage can be adjusted by the individual physician in the event of any contraindications. Dosage can vary, and can be administered in one or more dose administrations daily, for one or several days. Guidance can be found in the literature for appropriate dosages for given classes of pharmaceutical products. In further various aspects, a preparation can be administered in a "prophylactically effective amount"; that is, an amount effective for prevention of a disease or condition.

Effective dosages may be estimated initially from in vitro assays. For example, an initial dosage for use in animals may be formulated to achieve a circulating blood or serum concentration of active compound that is at or above an IC50 of the particular compound as measured in an in vitro assay. Calculating dosages to achieve such circulating blood or serum concentrations, taking into account the bioavailability of the particular active agent, is well within the capabilities of skilled artisans. For guidance, the reader is referred to Fingl & Woodbury, "General Principles," In: Goodman and Gilman's The Pharmaceutical Basis of Therapeutics, Chapter 1, pp. 1-46, latest edition, Pergamon Press, which is hereby incorporated by reference in its entirety, and the references cited therein.

The phrase "anti-cancer composition" can include compositions that exert antineoplastic, chemotherapeutic, antiviral, antimitotic, antitumorgenic, anti-angiogenic, antimetastatic and/or immunotherapeutic effects, e.g., prevent the development, maturation, or spread of neoplastic cells, directly on the tumor cell, e.g., by cytostatic or cytocidal effects, and not indirectly through mechanisms such as biological response modification. There are large numbers of anti-proliferative agents available in commercial use, in clinical evaluation and in pre-clinical development, which could be included in this application by combination drug chemotherapy. For convenience of discussion, anti-proliferative agents are classified into the following classes, subtypes and species: ACE inhibitors, alkylating agents, angiogenesis inhibitors, angiostatin, anthracyclines/DNA intercalators, anti-cancer antibiotics or antibiotic-type agents, antimetabolites, antimetastatic compounds, asparaginases, bisphosphonates, cGMP phosphodiesterase inhibitors, calcium carbonate, cyclooxygenase-2 inhibitors, DHA derivatives, DNA topoisomerase, endostatin, epipodophylotoxins, genistein, hormonal anticancer agents, hydrophilic bile acids (URSO), immunomodulators or immunological agents, integrin antagonists, interferon antagonists or agents, MMP inhibitors, miscellaneous antineoplastic agents, monoclonal antibodies, nitrosoureas, NSAIDs, ornithine decarboxylase inhibitors, pBATTs, radio/chemo sensitizers/protectors, retinoids, selective inhibitors of proliferation and migration of endothelial cells, selenium, stromelysin inhibitors, taxanes, vaccines, and vinca alkaloids.

The major categories that some anti-proliferative agents fall into include antimetabolite agents, alkylating agents, antibiotic-type agents, hormonal anticancer agents, immunological agents, interferon-type agents, and a category of miscellaneous antineoplastic agents. Some anti-proliferative agents operate through multiple or unknown mechanisms and can thus be classified into more than one category.

"Tilmanocept" refers to a non-radiolabeled precursor of the LYMPHOSEEK® diagnostic agent. Tilmanocept is a mannosylaminodextran (MAD). It has a dextran backbone to which a plurality of amino-terminated leashes (—$O(CH_2)_3S(CH_2)_2NH_2$) are attached to the core glucose elements. In addition, mannose moieties are conjugated to amino groups of a number of the leashes, and the chelator diethylenetriamine pentaacetic acid (DTPA) may be conjugated to the amino group of other leashes not containing the mannose. Tilmanocept generally, has a dextran backbone, in which a plurality of the glucose residues comprises an amino-terminated leash:

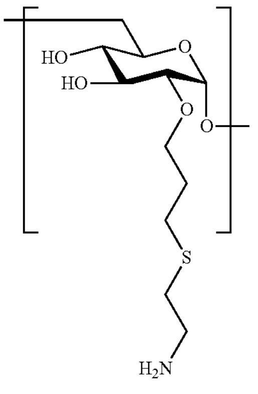

the mannose moieties are conjugated to the amino groups of the leash via an amidine linker:

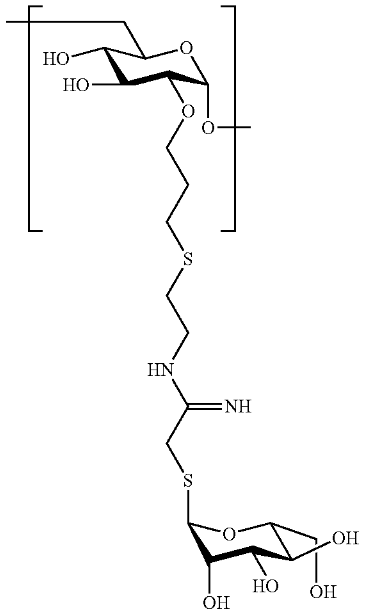

the chelator diethylenetriamine pentaacetic acid (DTPA) is conjugated to the amino groups of the leash via an amide linker:

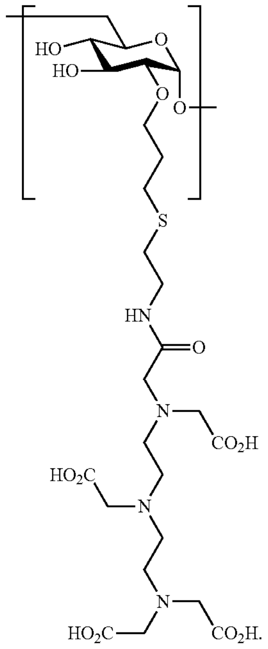

Tilmanocept has the chemical name dextran 3-[(2-aminoethyl)thio]propyl 17-carboxy-10,13,16-tris(carboxymethyl)-8-oxo-4-thia-7,10,13,16-tetraazaheptadec-1-yl 3-[[2-[[1-imino-2-(D-mannopyranosylthio)ethyl]amino]ethyl]thio]propyl ether complexes, and tilmanocept Tc99m has the following molecular formula: $[C_6H_{10}O_5]_n\cdot(C_{19}H_{28}N_4O_9S^{99m}Tc)_b\cdot(C_{13}H_{24}N_2O_5S_2)_c\cdot(C_5H_{11}NS)_a$ and contains 3-8 conjugated DTPA molecules (b); 12-20 conjugated mannose molecules (c); and 0-17 amine side chains (a) remaining free. Tilmanocept has the following general structure:

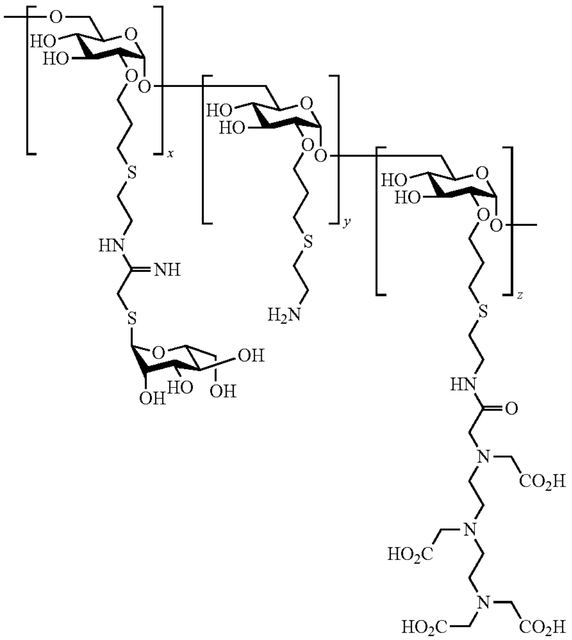

Certain of the glucose moieties may have no attached amino-terminated leash.

This instant disclosure describes compounds, compositions of matter, and methods for their use through altering the net charge of a mannosylated carbohydrate polymers for blocking (i.e. excluding through competition) the ability of MADs or other mannosylated carbohydrate polymers carrying diagnostic or therapeutic moieties to bind to C-type lectin receptor expressing cells in the liver, kidneys, and spleen, without proportionally diminishing the abilities of these MADs or other mannosylated carbohydrate polymers to bind to C-type lectin cells, for example, CD206 cells, that have aggregated at sites of pathological processes. CD206 is a transmembrane C-type lectin with high affinity for binding ligands displaying multiple terminal moieties of the sugar, mannose. CD206 also binds to ligands that display terminal moieties of the sugars, galactose, fucose, N-acetylgalactosamine (GalNAc), N-acetylglucosamine (GlcNAc), and/or glucuronic acid. CD206 is a cycling receptor that cycles between the cell surface and endosomes and releases its ligands into endosomes before recycling back to the cell surface. In addition, most of the CD206 molecules expressed by a cell are retained in an intracellular compartment and can be mobilized to the cells surface if CD206 molecules on the cell surface become depleted. These features of CD206 behavior may impact protocols in which two or more CD206 ligands are competing for binding to CD206 such that a competitor may need to be continuously or intermittently administered to prevent binding of alternative C-type lectin or CD206 ligand or ligands.

In further aspects, the leaky vasculature of tumors has been exploited by investigators as part of therapeutic strategies that attempt to use macromolecules, nanoparticles, or liposomes as drug delivery vehicles to increase the relative amounts of small molecule drugs delivered to tumors relative to that delivered to pathologically uninvolved tissues. However, there is another feature besides leaky vascularization that distinguishes cancerous tumors from healthy tissues. In some aspects, this distinguishing feature is that, for various physiological reasons, the extracellular spaces in tumors tend to be more acidic than blood or the extracellular spaces of pathologically uninvolved tissues. Importantly, it has been observed that acidic tumor environments limit the ability of polyanionic molecules (i.e., net negatively charged molecules), including drug delivery vehicles, to penetrate tumors due to repulsive electrostatic interactions. It has been observed that, when injected into the blood, twice as much of a polycationic (i.e., net positively charged molecule) will localize to a tumor compared to molecules of the same molecular weight that are either polyanionic or are electrostatically neutral.

A similar phenomenon, termed electrostatic hindrance, may be observed in the selective filtration of the glomerular membranes of the kidneys. Glomerular membranes are acidic due the abundance of acidic carbohydrates in their membrane structures. It has been observed that dextrans that have been chemically modified with basic moieties (i.e., to become polycations) transverse glomerular membranes more efficiently than neutral dextrans of similar molecular weights. Similarly, neutral dextrans transverse glomerular membranes more efficiently than dextrans of similar molecular weights modified with acid groups to become polyanions. Thus, when injected into the blood, more of a polycationic molecule will reach the mesangial cells than neutral or polyanionic molecules of similar size.

The present disclosure remedies the deficiencies in the art by synthesizing mannosylated carbohydrate polymers that have been modified to be either polyanionic (i.e., net negatively charged) or electrostatically neutral, and using these polyanionic or neutral mannosylated carbohydrate polymers as competitors for polycationic (i.e., net positively charged) mannosylated carbohydrate polymers carrying small molecule drug payloads or imaging moieties to CD206 expressing cells in target tissues, such as tumors or other sites of inflammation. The net positively charged MADs or mannosylated carbohydrate polymeric therapeutic or diagnostic compounds provide increased penetration into tumors and tissue, resulting in increased target specificity. In embodiments, a net negatively charged blocking compound and the net positively charged MADs or mannosylated carbohydrate polymeric therapeutic or diagnostic compounds are administered to a subject. In additional embodiments, the net positively charged mannosylated carbohydrate polymeric therapeutic or diagnostic compound is administered without the use of the blocking compound.

In an aspect, MAD constructs or mannosylated carbohydrate polymeric constructs retain unoccupied free amine terminated leashes at the conclusion of their syntheses. These free amine bases are predominantly protonated at physiological pH, resulting in MAD or carbohydrate polymer constructs carrying a weak net positive electrical charge (polycationic). The magnitude of the net positive charge on a MAD or carbohydrate polymer construct can be altered and controlled by varying the number of unoccupied free amine terminated leashes during the synthesis. Those with ordinary skill in the art will further appreciate that net positive charge can also be varied and controlled by synthesizing leashes that terminate with free amine or with other moieties that can be protonated at neutral or slightly acidic pH. In some embodiments, the net positive charge is varied and controlled by synthesizing leashes that terminate with more than one amine (polyamines), have highly basic amine functionality (i.e., guanidines), or are permanently charged quaternary ammonium salts. During the syntheses of MADs, the terminal carbon on the amine terminated leash may have two or three amine groups attached rather than one solitary amine, such as those used in the synthesis of tilmanocept, thereby increasing the net positive charge of the final mannosylated carbohydrate polymer constructs. Alternatively, the terminal amine groups of the unoccupied leashes may be capped with moieties that include tethered quaternary amines, which may also increase the net positive charge of the final mannosylated carbohydrate polymer constructs. Those skilled in the art will also appreciate that there are numerous other alternative chemical strategies that would increase the net positive charge on the final mannosylated carbohydrate polymer constructs.

In a further aspect, MADs or other mannosylated carbohydrate polymers can be synthesized to have net negative charges (i.e., polyanionic), especially at neutral or basic pH, by either synthesizing leashes that have terminal acidic groups, rather than terminal amines, or by capping the free amines with moieties that display a terminal acidic group. In certain aspects, the terminal acidic group may comprise carboxylate groups. In other aspects, the terminal acidic group may comprise carboxylate, sulfate, sulfonate, sulfinate, phosphate, phosphonate, or phosphinate moieties.

In other aspects, the MADs or other mannosylated carbohydrate polymers can be made neutral by adding a mannose moiety to all of the unoccupied free amine terminated leashes at the conclusion of their syntheses. Those with ordinary skill in the art will further appreciate that a mannosylated carbohydrate polymeric can be rendered neutral by appending any one of a wide variety of uncharged moieties to the unoccupied free amino terminated leashes that persist at the conclusion of syntheses. Appending the sugars galactose and/or fucose to the unoccupied amine terminated leashes are among the many mechanisms besides appending mannose by which the final MAD or mannosylated carbohydrate polymer constructs can be rendered neutral.

Chemically similar macromolecules having similar molecular weights, but a different net charge have different biodistributions when injected into a subject's bloodstream (i.e., by intravenous injection). Charge alters the biodistribution independently of size or other chemical features of MADs or mannosylated carbohydrate polymers. As such, the use of a blocking agent and a mannosylated carbohydrate polymer therapeutic or diagnostic compound having opposite charges (i.e., negative versus positive) will be suitable in increasing target specificity of the mannosylated carbohydrate polymeric therapeutic or diagnostic compound while reducing or eliminating off-target localization. In an aspect, the biodistributions of MADs or mannosylated carbohydrate polymerics have blood half-lives measured in minutes.

In certain aspects, a blocking agent having poor penetration into tumors and/or other target tissues will instead localize to Kupffer cells, splenic macrophages, and mesangial cells, as there are fewer (or no) barriers restricting their access to these cells. In a further aspect, a MAD construct or mannosylated dextran carrying a payload (drug or diagnostic moiety) and having a net positive charge opposite to that of the blocking agent will allow for more efficient localization, and less competition, to tumors and other targets of interest embedded in tissues. Such MAD constructs or mannosylated carbohydrate polymerics carrying a payload would therefore experience less competition in accessing CD206+ cells such as TAMs, dendritic cells, and MDSCs in tumors, resulting in maximized delivery of the payload or diagnostic moiety to the target while blocking off-target localization.

Blocking Compounds

In certain aspects, blocking compounds disclosed herein comprise a charged compound having the capability to bind to CD206. In exemplary embodiments, the blocking compounds are polyanionic or neutral, and synthesized to have a negative or neutral charge. The charge of the blocking compound is opposite to the charge of a mannosylated carbohydrate polymer therapeutic or diagnostic compound carrying a payload as further disclosed herein.

In additional aspects, the blocking compounds may employ a carrier construct comprising a polymeric (e.g. carbohydrate) backbone having conjugated thereto mannose-binding C-type lectin receptor targeting moieties (e.g. mannose) to preferentially bind to CD206, and at least one leash. In exemplary embodiments, the mannose-binding C-lectin type receptor targeting moieties bind to CD206 expressed in the kidney, liver, and/or spleen. Examples of such constructs include mannosylamino dextrans (MAD), which comprise a dextran backbone having mannose molecules conjugated to glucose residues of the backbone. In alternative embodiments, the blocking composition backbone may be comprised of any polymer suitable for safe administration to a subject and suitable for conjugation of C-lectin type receptor targeting moieties (with or without a leash). Examples include, but are not limited to cellulose, hyaluronic acid, chitosan, pullulan, and various polypeptides.

In certain aspects, the molecular weight (Mw) of the blocking compound can be varied and controlled by altering the molecular weight (Mw) of the starting dextran backbone on which it is constructed. In certain aspects, the dextran backbone of the blocking compound has a molecular weight of between about 1 and about 500 kDa, about 1 and about 450 kDa, about 1 and about 400 kDa, about 1 and about 350 kDa, about 1 and about 300 kDa, about 1 and about 250 kDa, about 1 and about 200 kDa, about 1 and about 150 kDa, about 1 and about 100 kDa, or about 1 and about 50 kDa. In additional embodiments, the backbone has a molecular weight of between about 1 and about 20 kDa, about 1 and about 15 kDa, about 1 and about 10 kDa, about 1 and about 5 kDa, while in other embodiments, the backbone has a molecular weight of between about 5 and about 40 kDa. In still other embodiments, the backbone has a molecular weight of between about 8 and about 15 kDa, such as about 10 kDa. While in other embodiments the backbone has a molecular weight of between about 1 and about 5 kDa, such as about 3.5 kDa. Beneficially, the molecular weight (Mw) of the various blocking compounds are smaller than the HMW-MAD constructs previously described in the art as blocking compounds.

In further embodiments, the polyanionic or neutral blocking compounds may have larger molecular weights than the polycationic mannosylated carbohydrate polymer carrying the small drug/therapeutic payload or imaging moiety. In some such embodiments, the polyanionic or neutral competitors may have molecular weights (Mw) in a range starting from about 20 kDa, while the polycationic mannosylated carbohydrate polymer carrying the small drug/therapeutic payload or imaging moiety may have a molecular weight (Mw) of about 10 kDa. Beneficially, the smaller molecular weight entity would diffuse more efficiently into the tumor tissue than the larger competitor, further enhancing the greater delivery of the cationic mannosylated carbohydrate polymer carrying the small drug/therapeutic payload or imaging moiety to the tumor.

In some embodiments, the mannose-binding C-type lectin receptor targeting moiety is selected from, but not limited to, mannose, galactose, fucose, N-acetylgalactosamine (GalNAc), N-acetylglucosamine (GlcNAc), and/or glucuronic acid. In some embodiments, the targeting moieties are attached to between about 10% and about 50% of the available residues of the blocking compound backbone, or between about 20% and about 45% of the residues, or between about 25% and about 40% of the residues.

According to certain embodiments, the one or more mannose-binding C-type lectin receptor targeting moieties are attached to the backbone by way of a leash. In some embodiments, the leash is an amino-terminated leash. In certain embodiments, the mannose-binding C-type lectin targeting moieties are attached to between about 15% and about 100%, between about 17% and about 65%, or about 20% and about 60% of the glucose residues via the amino terminated leashes. In further embodiments, the mannose-binding C-type lectin targeting moieties are attached to up to about 60%, up to about 70%, up to about 80%, up to about 90%, or up to about 100% of the glucose residues via the amino terminated leashes. In certain aspects, the percentages may vary depending on the size of the carbohydrate polymer backbone.

In aspects, the leash may be attached to from about 30% to about 100% of the backbone moieties, or from about 70% to about 90% of the backbone moieties. The leashes may be the same or different. In some embodiments, the leashes may comprise the formula $-(CH_2)_pS(CH_2)_q-NH-$, wherein p and q are integers from 0 to 5. In further embodiments, the leash comprises the formula $-(CH_2)_3S(CH_2)_2NH-$. In embodiments where the leash is not attached to a mannose-binding C-type lectin receptor targeting moiety, the leash may comprise the formula $-(CH_2)_pS(CH_2)_q-NH_2$, wherein p and q are integers from 0 to 5.

In some embodiments, the leash may be a chain of from 1 to 20 member atoms selected from carbon, oxygen, sulfur, nitrogen and phosphorus. The leash may be a straight chain or branched. The leash may also be substituted with one or more substituents including, but not limited to, halo groups, perfluoroalkyl groups, perfluoroalkoxy groups, alkyl groups, such C1-4 alkyl, alkenyl groups, such as C1-4 alkenyl, alkynyl groups, such as C1-4 alkynyl, hydroxy groups, oxo groups, mercapto groups, alkylthio groups, alkoxy groups, nitro groups, azidealkyl groups, aryl or heteroaryl groups, aryloxy or heteroaryloxy groups, aralkyl or heteroaralkyl groups, aralkoxy or heteroaralkoxy groups, HO—(C═O)— groups, heterocylic groups, cycloalkyl groups, amino groups, alkyl- and dialkylamino groups, carbamoyl groups, alkylcarbonyl groups, alkylcarbonyloxy groups, alkoxycarbonyl groups, alkylaminocarbonyl groups, dialkylamino carbonyl groups, arylcarbonyl groups, aryloxycarbonyl groups, alkylsulfonyl groups, arylsulfonyl groups, —NH—NH2; ═N—H; ═N-alkyl; —SH; —S-alkyl; —NH—C(O)—; —NH—C(═N)— and the like. As would be apparent to one skilled in the art, other suitable leashes are possible. In certain alternative embodiments, the targeting moiety is attached directly to the backbone without use of a leash. In other embodiments, the mannose-binding C-type lectin targeting moieties may be conjugated to the amino groups of the amino terminated leash via an amidine and/or amide linker.

In an aspect, the charge of the blocking compound is modified via the leashes. As already described in further detail herein, the charge of the blocking compounds may be synthesized to have net negative charges (i.e., are polyanionic), especially at neutral or basic pH, by either synthesizing leashes that have terminal acidic groups, rather than terminal amines, or by capping the free amines with moieties that display a terminal acidic group. In certain aspects, the terminal acidic group may comprise carboxylate groups. In other aspects, the terminal acidic group may comprise carboxylate, sulfate, sulfonate, sulfinate, phosphate, phosphonate, or phosphinate moieties. In embodiments, the leashes modified for purposes of altering the charge of the mannosylated carbohydrate polymers may have the following formula: $-(CH_2)_pS(CH_2)_q-NH-Y$, wherein p and q are integers from 0 to 5, and wherein Y comprises the terminal acidic groups comprising a carboxylate, sulfate, sulfonate, sulfinate, phosphate, phosphonate, or phosphinate moiety.

In other aspects, the MADs or other mannosylated carbohydrate polymers can be made neutral by adding a mannose moiety to all of the unoccupied free amine terminated leashes at the conclusion of their syntheses. Those with ordinary skill in the art will further appreciate that a mannosylated carbohydrate polymeric can be rendered neutral by appending any one of a wide variety of uncharged moieties to the unoccupied free amino terminated leashes that persist at the conclusion of syntheses. Appending the sugars galactose and/or fucose to the unoccupied amine terminated leashes are among the many mechanisms besides appending mannose by which the final MAD or mannosylated carbohydrate polymer constructs can be rendered neutral. In embodiments, the leashes modified for purposes of altering the charge of the mannosylated carbohydrate polymers may have the following formula: $-(CH_2)_pS(CH_2)_q-NH-Y$, wherein p and q are integers from 0 to 5, and wherein Y comprises a terminal neutral group comprising the mannose moiety.

According to certain embodiments, blocking compound comprises the compound of Formula (II):

(II)

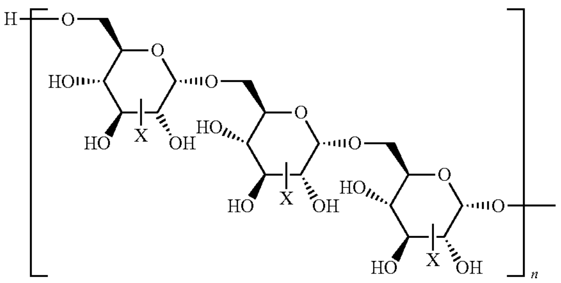

wherein each X is H, L1-R, or L2-Y;

each L1 and L2 are independently leashes;

each R independently comprises a mannose-binding C-type lectin receptor targeting moiety or H; and each Y independently comprises a carboxylate, sulfate, sulfonate, sulfinate, phosphate, phosphonate, phosphinate, or mannose moiety, or H; and n is an integer greater than zero, wherein each unit of n may be the same or different.

In some embodiments, at least one R of formula (II) comprises a mannose-binding C-type lectin receptor targeting moiety selected from the group consisting of mannose, galactose, fucose, N-acetylgalactosamine (GalNAc), N-acetylglucosamine (GlcNAc), and/or glucuronic acid.

In some aspects, the leashes may be any leash as further described herein. In some embodiments, both leashes L1 and L2 are amino terminated leashes, wherein the amino terminated leashes may comprise the formula $-(CH_2)_pS(CH_2)_q-NH-$, wherein p and q are integers from 0 to 5.

In some aspects, n is an integer greater than zero. In other aspects, n is an integer greater than 1. In further aspects, n may be an integer between 1 and about 50, between about 5 and about 40, or between about 5 and about 30. As would be understood by those skilled in the art, each unit of n may be the same or may be different. As each X may independently be H, L1-R, or L2-Y, each unit of n may consist of any combination of X selected from H, L1-R, or L2-Y.

In some aspects, at least one Y comprises a terminal acidic group comprising a carboxylate, sulfate, sulfonate, sulfinate, phosphate, phosphonate, or phosphinate moiety. By way of example only, the blocking compound may comprise a unit n wherein at least one Y is a terminal acidic group comprising a sulfonate moiety as shown in formula (IIa). In a further example, the blocking compound may comprise a unit n wherein at least one Y is a terminal acidic group comprising a carboxylate moiety as shown in formula (IIb):

(IIa)

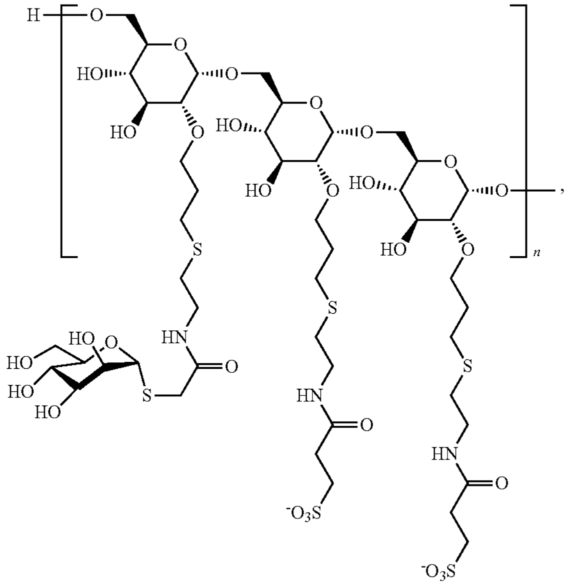

(IIb)

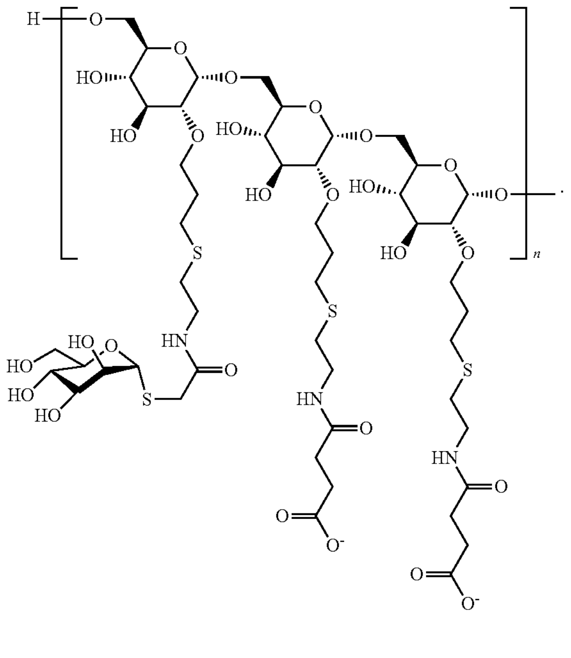

In some aspects, when at least one Y comprises a terminal neutral group comprising the mannose moiety, every Y present within the compound of formula (II) must comprise the mannose moiety. This ensures that the blocking compound remains neutral in charge. By way of example only, the blocking compound may comprise a unit n wherein each Y present is the mannose moiety as shown in formula (IIc):

(IIc)

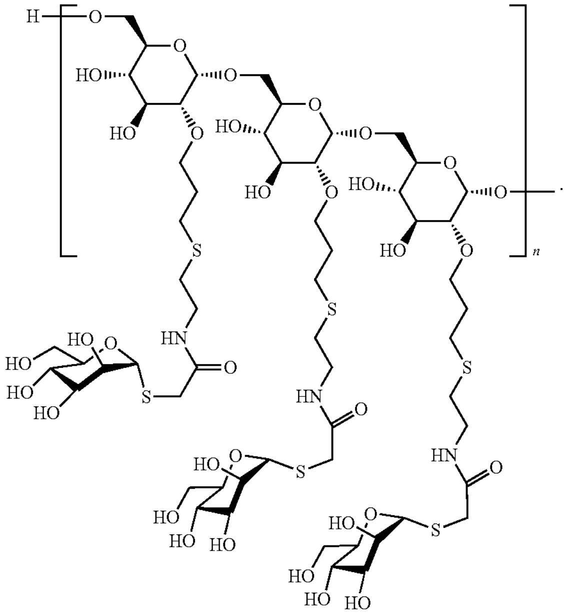

Mannosylated Carbohydrate Polymeric Therapeutic or Diagnostic Compounds

In certain aspects, compounds disclosed herein employ a carrier construct comprising a carbohydrate polymeric backbone having conjugated thereto mannose-binding C-type lectin receptor targeting moieties (e.g., mannose, fucose, and N-acetylglucosamine) to deliver one or more active therapeutic agents or diagnostic agents. Examples of such constructs include mannosylamino dextrans (MAD), which comprise a dextran backbone having mannose molecules conjugated to glucose residues of the backbone and having an active pharmaceutical ingredient conjugated to glucose residues of the backbone. Tilmanocept is a specific example of an MAD. A tilmanocept derivative that is tilmanocept without DTPA conjugated thereto is a further example of an MAD. In certain aspects, the carbohydrate polymer therapeutic or diagnostic compound disclosed herein comprise a charged compound. In exemplary embodiments, the carbohydrate polymer therapeutic or diagnostic compounds are polycationic and synthesized to have a positive charge.

In certain implementations, the disclosure provides a compound comprising a dextran-based moiety or backbone having one or more mannose-binding C-type lectin receptor targeting moieties and one or more therapeutic agents attached thereto. In an aspect, the compound is charged to provide increased penetration to tumors and other target tissues. The dextran-based moiety generally comprises a dextran backbone similar to that described in U.S. Pat. No. 6,409,990 (the '990 patent), which is incorporated herein by reference. Thus, the backbone comprises a plurality of glucose moieties (i.e., residues) primarily linked by α-1,6 glycosidic bonds. Other linkages such as α-1,4 and/or α-1,3 bonds may also be present. In some embodiments, not every backbone moiety is substituted. In some embodiments, mannose-binding C-type lectin receptor targeting moieties are attached to between about 10% and about 50% of the glucose residues of the dextran backbone, or between about 20% and about 45% of the glucose residues, or between about 25% and about 40% of the glucose residues. In some embodiments, the dextran backbone has a molecular weight of between about 1 and about 500 kDa, about 1 and about 450 kDa, about 1 and about 400 kDa, about 1 and about 350 kDa, about 1 and about 300 kDa, about 1 and about 250 kDa, about 1 and about 200 kDa, about 1 and about 150 kDa, about 1 and about 100 kDa, or about 1 and about 50 kDa. In additional embodiments, the backbone has a molecular weight of between about 1 and about 20 kDa, about 1 and about 15 kDa, about 1 and about 10 kDa, about 1 and about 5 kDa, while in other embodiments the backbone has a molecular weight of between about 5 and about 40 kDa. In still other embodiments, the backbone has a molecular weight of between about 8 and about 15 kDa, such as about 10 kDa. While in other embodiments the backbone has a molecular weight of between about 1 and about 5 kDa, such as about 2 kDa.

According to further aspects, the mannose-binding C-type lectin receptor targeting moiety is selected from, but not limited to, mannose, galactose, fucose, N-acetylgalactosamine (GalNAc), N-acetylglucosamine (GlcNAc), and/or glucuronic acid. In some embodiments, the targeting moieties are attached to between about 10% and about 50% of the glucose residues of the dextran backbone, or between about 20% and about 45% of the glucose residues, or between about 25% and about 40% of the glucose residues. MWs referenced herein, as well as the number and degree of conjugation of receptor substrates, leashes, and diagnostic/therapeutic moieties attached to the dextran backbone refer to average amounts for a given quantity of carrier molecules, since the synthesis techniques will result in some variability.

According to certain embodiments, the one or more mannose-binding C-type lectin receptor targeting moieties and one or more therapeutic or diagnostic agents are attached to the dextran-based moiety by way of a leash. The leash may be attached at from about 50% to about 100% of the backbone moieties or about 70% to about 90%. The leashes may be the same or different. In some embodiments, the leash is an amino-terminated leash. The leashes may be the same or different. In some embodiments, the leashes may comprise the formula $-(CH_2)_pS(CH_2)_q-NH-$, wherein p and q are integers from 0 to 5. In further embodiments, the leash comprises the formula $-(CH_2)_3S(CH_2)_2NH-$. In embodiments where the leash is not attached to a mannose-binding C-type lectin receptor targeting moiety, the leash may comprise the formula $-(CH_2)_pS(CH_2)_q-NH_2$, wherein p and q are integers from 0 to 5. In some embodiments, the leashes may comprise $-O(CH_2)_3S(CH_2)_2NH-$. In some embodiments, the leash may be a chain of from 1 to 20 member atoms selected from carbon, oxygen, sulfur, nitrogen and phosphorus. The leash may be a straight chain or branched. The leash may also be substituted with one or more substituents including, but not limited to, halo groups, perfluoroalkyl groups, perfluoroalkoxy groups, alkyl groups, such C1-4 alkyl, alkenyl groups, such as C1-4 alkenyl, alkynyl groups, such as C1-4 alkynyl, hydroxy groups, oxo groups, mercapto groups, alkylthio groups, alkoxy groups, nitro groups, azidealkyl groups, aryl or heteroaryl groups, aryloxy or heteroaryloxy groups, aralkyl or heteroaralkyl groups, aralkoxy or heteroaralkoxy groups, HO—(C=O)— groups, heterocylic groups, cycloalkyl groups, amino groups, alkyl- and dialkylamino groups, carbamoyl groups, alkylcarbonyl groups, alkylcarbonyloxy groups, alkoxycarbonyl groups, alkylaminocarbonyl groups, dialkylamino carbonyl groups, arylcarbonyl groups, aryloxycarbonyl groups, alkylsulfonyl groups, arylsulfonyl groups, $-NH-NH_2$; =N—H; =N-alkyl; —SH; —S-alkyl; —NH—C(O)—; —NH—C(=N)— and the like. As would be apparent to one skilled in the art, other suitable leashes are possible. In other embodiments, the mannose-binding C-type lectin targeting moieties may be conjugated to the amino groups of the amino terminated leash via an amidine and/or amide linker.

In an aspect, the charge of the mannosylated carbohydrate polymeric therapeutic and diagnostic compounds is modified via the leashes. As already described in further detail herein, in some embodiments, the net positive charge may be varied and controlled by synthesizing leashes that terminate with more than one amine (polyamines), have highly basic amine functionality (i.e., guanidines), or are permanently charged quaternary ammonium salts. In embodiments, the leashes modified for purposes of altering the charge of the mannosylated carbohydrate polymeric therapeutic and diagnostic compounds may have the following formula: $-(CH_2)_pS(CH_2)_q-W$, wherein p and q are integers from 0 to 5, and wherein W comprises the terminal amine groups comprising linear or branched polyamine, guanidine, or quaternary ammonium moieties.

By way of example only, the mannosylated carbohydrate polymeric therapeutic and diagnostic compound may include terminal amine groups comprising example linear or branched polyamine moieties as follows:

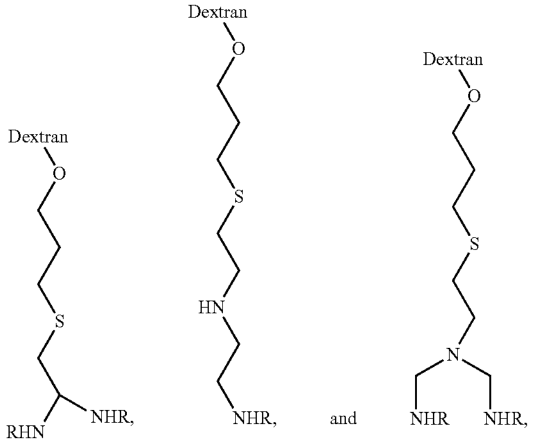

wherein R is H, alkyl, or alkyl amine. As would be appreciated by those skilled in the art, other linear or branched polyamines may be considered and utilized in the compounds, compositions, and methods of the present disclosure.

In a further example, the mannosylated carbohydrate polymeric therapeutic and diagnostic compound may include terminal amine groups comprising the guanidine moiety as follows:

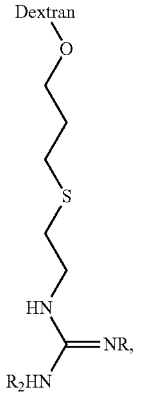

wherein R is H, alkyl, or alkyl amine. As would be appreciated by those skilled in the art, other moieties having highly basic amine functionality may be considered and utilized in the compounds, compositions, and methods of the present disclosure.

In a further example, the mannosylated carbohydrate polymeric therapeutic and diagnostic compound may include terminal amine groups comprising quaternary ammonium moieties as follows:

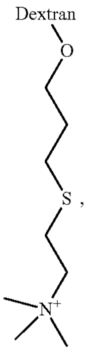 , and 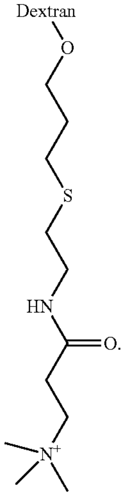 .

As would be appreciated by those skilled in the art, other quaternary ammonium moieties may be considered and utilized in the compounds, compositions, and methods of the present disclosure.

In some embodiments, the one or more therapeutic agents is attached via a biodegradable linker. In some embodiments, the biodegradable linker comprises a pH sensitive moiety, such as a hydrazone. At lower (more acidic) pH, hydrazone linkers spontaneously hydrolyze at increasing rates as pH decreases. When a mannosylated carbohydrate polymeric binds to CD206, it is internalized to endosomes which become increasingly acidified over time, thereby releasing the therapeutic agent payloads intracellularly.

According to further embodiments, the therapeutic agent is a cytotoxic agent (e.g. doxorubicin). In still further embodiments, the therapeutic agent is an anti-cancer agent.

In certain aspects, a chelating agent may be attached to or incorporated into a disclosed compound, and used to chelate a therapeutic agent, such as Cu(II). Exemplary chelators include but are not limited to DTPA (such as Mx-DTPA), DOTA, TETA, NETA or NOTA. According to certain exemplary implementations, the chelator is DOTA.

Any of a variety of detectable moieties can be attached to the carrier molecule, directly or indirectly, for a variety of purposes. As used herein, the term “detectable moiety” or “diagnostic moiety” (which these terms may be used interchangeably) means an atom, isotope, or chemical structure which is: (1) capable of attachment to the carrier molecule; (2) non-toxic to humans; and (3) provides a directly or indirectly detectable signal, particularly a signal which not only can be measured but whose intensity is related (e.g., proportional) to the amount of the detectable moiety. The signal may be detected by any suitable means, including spectroscopic, electrical, optical, magnetic, auditory, radio signal, or palpation detection means as well as by the measurement processes described herein.

Suitable detectable moieties include, but are not limited to radioisotopes (radionuclides), fluorophores, chemiluminescent agents, bioluminescent agents, magnetic moieties (including paramagnetic moieties), metals (e.g., for use as contrast agents), RFID moieties, enzymatic reactants, colorimetric release agents, dyes, and particulate-forming agents.

By way of specific example, suitable diagnostic moieties include, but are not limited to:

- contrast agents suitable for magnetic resonance imaging (MRI), such as gadolinium (Gd3+), paramagnetic and superparamagnetic materials such as superparamagnetic iron oxide;
- contrast agents suitable for computed tomographic (CT) imaging, such as iodinated molecules, ytterbium and dysprosium;
- radioisotopes suitable for scintigraphic imaging (or scintigraphy) such as $^{99m}$Tc, $^{210/212/213/214}$Bi, $^{131}$Ba, $^{140}$Ba, $^{11/14}$C, $^{51}$Cr, $^{67/68}$Ga, $^{153}$Gd, $^{88/90/91}$Y, $^{123/124/125/131}$I, $^{111/115m}$In, $^{18}$F, $^{13}$N, $^{105}$Rh, $^{153}$Sm, $^{67}$Cu, $^{166}$Ho, $^{177}$Lu, $^{223}$Ra, $^{62}$Rn, $^{186/188}$Re, $^{32/33}$P, $^{46/47}$Sc, $^{72/75}$Se, $^{35}$S, $^{89}$Sr, $^{182}$Ta, $^{123m}$Te, $^{127}$Te, $^{129}$Te, $^{132}$Te, $^{65}$Zn, $^{89/95}$Zr; or other chelateable isotope(s);
- gamma-emitting agents suitable for single-photon emission computed tomography (SPECT), such as $^{99m}$Tc, $^{111}$In, and $^{123}$I;
- dyes and fluorescent agents suitable for optical imaging; and
- agents suitable for positron emission tomography (PET) such as $^{18}$F.

A diagnostic moiety can be attached to the carrier molecule in a variety of ways, such as by direct attachment or using a chelator attached to a carrier molecule. In some embodiments, diagnostic moieties can be attached using leashes attached to a carrier backbone. In some embodiments, the chelator can be conjugated to an amino group of one or more leashes and can be used to bind the diagnostic moiety thereto. It should be noted that in some instances, glucose moieties of the carbohydrate polymeric backbone may have no attached leash. Certain embodiments may include a single type of diagnostic moiety or a mixture of different diagnostic moieties. For example, an embodiment of a compound disclosed herein may comprise a contrast agent suitable for MRI and a radioisotope suitable for scintigraphic imaging, and further combinations of the diagnostic moieties described herein.

One or more diagnostic moieties can be attached to the one or more leashes using a suitable chelator. Suitable chelators include ones known to those skilled in the art or hereafter developed, such as, for example but without limitation, tetraazacyclododecanetetraacetic acid (DOTA), mercaptoacetylglycylglycyl-glycine (MAG3), diethylenetriamine pentaacetic acid (DTPA), dimercaptosuccinic acid, diphenylethylene diamine, porphyrin, iminodiacetic acid, and ethylenediaminetetraacetic acid (EDTA).

In certain aspects, the disclosed compounds are present in the form of a pharmaceutically acceptable carrier.

According to certain embodiments, the disclosed carbohydrate polymeric therapeutic or diagnostic compound is a compound of Formula (I):

(I)

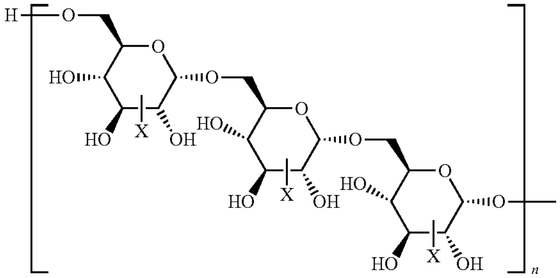

wherein each X is independently H, L1-A, L2-R, L3-W, or L4-A-W;

- each L1, L2, L3, and L4 are independently leashes;
- each A independently comprises a therapeutic agent, diagnostic agent, or H;
- each R independently comprises a mannose-binding C-type lectin receptor targeting moiety or H;
- each W is independently a terminal amine group comprising a linear or branched polyamine, guanidine, or quaternary ammonium moiety; and
- n is an integer greater than zero, wherein each unit of n may be the same or different; and
- wherein at least one R comprises a mannose-binding C-type lectin receptor targeting moiety selected from the group consisting of mannose, galactose, fucose, N-acetylgalactosamine (GalNAc), N-acetylglucosamine (GlcNAc), and/or glucuronic acid, and at least one A comprises a therapeutic agent or diagnostic agent.

In certain embodiments, each of L1, L2, and L4 comprises the formula $-(CH_2)_pS(CH_2)_q-NH-$, wherein p and q are independently integers from 0 to 5.

According to further embodiments, at least one of L1, L2, or L4 is a C2-12 hydrocarbon chain optionally interrupted by up to three heteroatoms selected from the group consisting of O, S and N.

In certain embodiments, each of L3 comprises the formula $-(CH_2)_pS(CH_2)_q-W$, wherein p and q are independently integers from 0 to 5, and wherein W comprises the terminal amine groups comprising a linear or branched polyamine, guanidine, or quaternary ammonium moiety.

In some aspects, n is an integer greater than zero. In other aspects, n is an integer greater than 1. In further aspects, n may be an integer between 1 and about 50, between about 5 and about 40, or between about 5 and about 30. As would be understood by those skilled in the art, each unit of n may be the same or may be different. As each X may independently be H, L1-A, L2-R, L3-W, or L4-A-W, each unit of n may consist of any combination of X selected from H, L1-A, L2-R, L3-W, or L4-A-W.

By way of example only, the mannosylated carbohydrate polymeric therapeutic and diagnostic compound may comprise a unit n wherein at least one W comprises the quaternary ammonium moiety as shown in formula (Ia) to provide a positive charge to the compound:

(Ia)

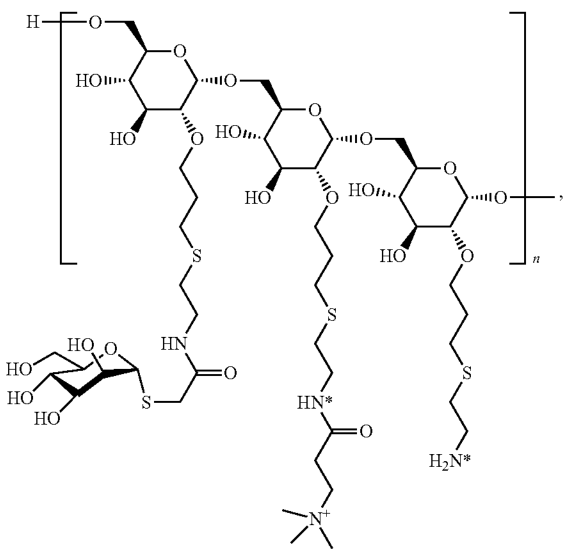

wherein the * indicates the point at which the therapeutic agent or diagnostic agent is attached. In certain embodiments, the therapeutic agent or diagnostic agent is attached at the end of an amino-terminated leash with or without a linker. In further embodiments, the therapeutic agent or diagnostic agent may be attached at the end of the amino-terminated leash, with a terminal amine group comprising a linear or branched polyamine, guanidine, or quaternary ammonium moiety further appended to the therapeutic or diagnostic agent.

According to certain embodiments, the disclosed compounds (e.g., the mannosylated carbohydrate polymeric therapeutic or diagnostic compound and/or the blocking compound) or a pharmaceutically acceptable salt of the compounds, can include a pharmaceutically acceptable carrier. The disclosed compounds, or pharmaceutically acceptable salts thereof, can also be included in pharmaceutical compositions in combination with one or more other therapeutically active compounds. In an aspect, the mannosylated carbohydrate polymeric therapeutic or diagnostic compound is administered with or shortly after the administration of a blocking compound. In additional aspects, the mannosylated carbohydrate polymeric therapeutic or diagnostic compound is administered without the use of a blocking compound.

Therapeutic Compositions

According to certain embodiments, the disclosed mannosylated carbohydrate polymeric therapeutic or diagnostic compounds are further provided in a therapeutic composition. In embodiments, the disclosed mannosylated carbohydrate polymeric therapeutic or diagnostic compounds are charged. In additional aspects, the charged mannosylated carbohydrate polymeric therapeutic or diagnostic compounds are provided with blocking compounds in a therapeutic composition. In an aspect, the compositions may optionally further comprise a pharmaceutically acceptable carrier.

In embodiments, the pharmaceutically acceptable carrier employed may be, for example, a solid, liquid, or gas. Examples of solid carriers include lactose, terra alba, sucrose, talc, gelatin, agar, pectin, acacia, magnesium stearate, and stearic acid. Examples of liquid carriers are sugar syrup, peanut oil, olive oil, and water. Examples of gaseous carriers include carbon dioxide and nitrogen.

In preparing the compositions into a dosage form, any convenient pharmaceutical media can be employed. For example, water, glycols, oils, alcohols, flavoring agents, preservatives, coloring agents and the like can be used to form oral liquid preparations such as suspensions, elixirs and solutions; while carriers such as starches, sugars, microcrystalline cellulose, diluents, granulating agents, lubricants, binders, disintegrating agents, and the like can be used to form oral solid preparations such as powders, capsules and tablets. Because of their ease of administration, tablets and capsules are the preferred oral dosage units whereby solid pharmaceutical carriers are employed. Optionally, tablets can be coated by standard aqueous or nonaqueous techniques. In certain aspects, the compositions are administered intravenously, intraperitoneally, intramuscularly, orally, subcutaneously, intra-tumorally or transdermally.

Methods of Use

According to certain embodiments, disclosed is a method for increasing target specificity of a mannosylated carbohydrate polymeric therapeutic or diagnostic compound by administering at least one blocking compound. In certain aspects, disclosed is a method for increasing target specificity of a mannosylated carbohydrate polymeric therapeutic or diagnostic compound by administering a blocking compound comprising a backbone, and one or more CD206 targeting moieties attached thereto; and administering an effective amount of the mannosylated carbohydrate polymeric therapeutic or diagnostic compound comprising a dextran backbone and one or more CD206 targeting moieties and one or more therapeutic agents attached thereto, wherein the blocking compound and the mannosylated carbohydrate polymeric therapeutic or diagnostic compound have different net charges as described herein (i.e., the therapeutic or diagnostic mannosylated carbohydrate polymer would be polycationic (net positive charge) while the competitive blocking mannosylated carbohydrate polymer would be polyanionic (net negative charge) or neutral).

In an embodiment, the varying net charges of the competitive blocking compound and mannosylated carbohydrate polymeric therapeutic or diagnostic compound are altered via a leash. In an aspect, the leash is an amino-terminated leash. In an aspect, these free amines of the amino-terminated leash can become protonated, especially at neutral or acidic pH, resulting in compounds with weak net positive electrical charges. In a further aspect, and as already described herein, net negative charges can be displayed on the carbohydrate polymer backbone, either by synthesizing leashes that have terminal acidic groups, or by capping the amine terminated leashes with moieties that display a terminal acidic group. In certain aspects, the terminal acidic group may comprise carboxylate groups. As already further described herein, neutral competitive blocking agents can be synthesized by exhaustively adding mannose moieties or other neutral moieties to the free amine terminated leashes that remain after completion of syntheses.

In exemplary implementations, the net charge of the mannosylated carbohydrate polymeric therapeutic or diagnostic compound is positive, which is opposite to the charge of the blocking compound which can be negative or neutral. In additional embodiments, the method comprises increasing target specificity of a mannosylated carbohydrate polymeric therapeutic or diagnostic compound by altering the charge on the compound to have a net positive charge. The method comprises administering an effective amount of the charged mannosylated carbohydrate polymeric therapeutic or diagnostic compound comprising a carbohydrate polymeric backbone and one or more CD206 targeting moieties and one or more therapeutic agents attached thereto.

In certain aspects, the blocking compound is administered at about the same time as the mannosylated carbohydrate polymeric therapeutic or diagnostic compound. In alternative aspects, the step of administering the blocking compound is followed by a time interval before the administration of the mannosylated carbohydrate polymeric therapeutic or diagnostic compound. According to these embodiments, during this time interval, the block compound circulates throughout the body of the subject and binds to off-target CD206 expressing cells in the kidney, liver, spleen, or combination thereof to allow for subsequent competitive exclusion of the mannosylated carbohydrate polymeric therapeutic or diagnostic compound from binding to such cells. In certain aspects, the time interval is at least about ten minutes. In further aspects, the time interval is between 0 minutes and about 60 minutes. In further aspects, the time interval is from 10 minutes to about 30 minutes. In still further aspects, the time interval is from 10 minutes to about 20 minutes.

In additional embodiments, a polyanionic or neutral mannosylated carbohydrate polymeric blocking compound would be administered simultaneously or shortly administration of a polycationic mannosylated carbohydrate polymer carrying a drug payload or imaging moiety. The competitor would be administered at a molar excess to the dose of the polycationic mannosylated carbohydrate polymer carrying the small drug payload or imaging moiety. In this case, the blocking agent (i.e. competitor) would freely bind to CD206 expressed on Kupffer cells of the liver, macrophages of the spleen and to mesangial cells of the kidneys because of the limited barriers between the blood flow and these cells types. This competition would prevent or limit the ability of the polycationic mannosylated carbohydrate polymer carrying the small drug payload or imaging moiety from binding to these cells.

Conversely, the polycationic mannosylated carbohydrate polymer carrying the small drug payload or imaging moiety would preferentially localize to CD206 expressed on TAMs in tumors because of the repulsive electrostatic effects derived from the acidic nature of the tumor's extracellular spaces. This would enable delivery of equal or greater amounts of the small molecule drug payload or imaging moiety to the tumors (TAMs, dendritic cells, and MDSC) while less would be localized to Kupffer cells, mesangial cells, and splenic macrophages than would occur using competitive protocols described in the art. In some embodiments, a neutral competitor may be preferred to an anionic competitor to enable greater competitive blocking of the mesangial cells. In some embodiments, the competitive polyanionic or neutral mannosylated dextran competitors could be administered at doses of from about 2 to about 20 times the mass dose of the polycationic mannosylated carbohydrate polymer carrying the small drug payload or imaging moiety. In some other embodiments, the competitive polyanionic or neutral mannosylated carbohydrate polymer blocking compounds may be administered at doses of from about 5 to about 10 times the mass dose of the cationic mannosylated carbohydrate polymer carrying the small drug payload or imaging moiety.

According to certain embodiments of the disclosed method, the mannosylated carbohydrate polymeric therapeutic or diagnostic compound comprises at least one therapeutic moiety. In certain exemplary implementations of these embodiments, the effective dose of the mannosylated carbohydrate polymeric therapeutic or diagnostic compound is lower than the effective dose of the mannosylated carbohydrate polymeric therapeutic or diagnostic compound without administration of the blocking compound.

According to further embodiments, the blocking compound preferentially binds to CD206 expressing cells in the liver, kidney, and/or spleen. In exemplary implementations, the mannosylated carbohydrate polymeric therapeutic or diagnostic compound has decreased binding to CD206 cells in the liver, kidney, and/or spleen relative to a subject administered a comparable dose of mannosylated carbohydrate polymeric therapeutic or diagnostic compound without administration of the blocking compound.

In certain aspects, the compound is administered in a therapeutically effective amount. The compound is administered in prophylactically effective amount.

In certain aspects, the method further comprises administering the composition as a bolus and/or at regular intervals. In certain aspects, the disclosed method further comprises administering the composition intravenously, intraperitoneally, intramuscularly, orally, subcutaneously, intraocularly, intra-tumor injection or transdermally or delivered directly to tumor organ by invasive techniques.

In embodiments, the polyanionic or neutral competitor blocking compounds may be administered intravenously as continuous infusions to ensure there is always a sufficient amount of the competitor or blocking compound to occupy the continuously-replenished CD206 receptors in the off-target organs while the polycationic mannosylated carbohydrate polymer carrying the small drug/therapeutic payload or imaging moiety remains in the blood circulation. In some embodiments, the infusion of the competitors may continue for an interval of between about 10 minutes to about 1 hour, between about 15 minutes and 45 minutes, or about 20 minutes to 40 minutes after the polycationic mannosylated carbohydrate polymer carrying the small drug/therapeutic payload or imaging moiety has been injected intravenously.

The methods provided herein may be practiced in an adjuvant setting. In some embodiments, the method is practiced in a neoadjuvant setting, i.e., the method may be carried out before the primary/definitive therapy. In some embodiments, the method is used to treat an individual who has previously been treated. Any of the methods of treatment provided herein may be used to treat an individual who has not previously been treated. In some embodiments, the method is used as a first line therapy. In some embodiments, the method is used as a second line therapy.

According to certain aspects, the subject has been diagnosed with melanoma, breast cancer, lung carcinoma, pancreatic carcinoma, renal carcinoma, ovarian, prostate or cervical carcinoma, glioblastoma, or colorectal carcinoma, cerebrospinal tumor, head and neck cancer, thymoma, mesothelioma, esophageal cancer, stomach cancer, liver cancer, pancreatic cancer, bile duct cancer, bladder cancer, testicular cancer, germ cell tumor, ovarian cancer, uterine cervical cancer, endometrial cancer, lymphoma, acute leukemia, chronic leukemia, multiple myeloma, sarcoma, or any combination thereof.

According to certain further embodiments, the method further comprises diagnosing the subject with cancer. In further aspects, the subject is diagnosed with cancer prior to administration of the composition. According to still further aspects, the method further comprises evaluating the efficacy of the composition. In yet further aspects, evaluating the efficacy of the composition comprises measuring tumor size prior to administering the composition and measuring tumor size after administering the compound. In even further aspects, evaluating the efficacy of the composition occurs at regular intervals. According to certain aspects, the disclosed method further comprises optionally adjusting at least one aspect of method. In yet further aspects, adjusting at least one aspect of method comprises changing the dose of the composition, the frequency of administration of the composition, or the route of administration of the compound.

According to certain alternative embodiments, the subject has been diagnosed with a disease associated with elevated levels of CD206+ macrophages and/or MDSC. Such diseases or conditions include, but are not limited to: acquired immune deficiency syndrome (AIDS), acute disseminated encephalomyelitis (ADEM), Addison's disease, agammaglobulinemia, allergic diseases, alopecia areata, Alzheimer's disease, amyotrophic lateral sclerosis, ankylosing spondylitis, antiphospholipid syndrome, antisynthetase syndrome, arterial plaque disorder, asthma, atherosclerosis, atopic allergy, atopic dermatitis, autoimmune aplastic anemia, autoimmune cardiomyopathy, autoimmune enteropathy, autoimmune hemolytic anemia, autoimmune hepatitis, autoimmune hypothyroidism, autoimmune inner ear disease, autoimmune lymphoproliferative syndrome, autoimmune peripheral neuropathy, autoimmune pancreatitis, autoimmune polyendocrine syndrome, autoimmune progesterone dermatitis, autoimmune thrombocytopenic purpura, autoimmune urticarial, autoimmune uveitis, Balo disease/Balo concentric sclerosis, Behcet's disease, Berger's disease, Bickerstaffs encephalitis, Blau syndrome, bullous pemphigoid, Castleman's disease, celiac disease, Chagas disease, chronic inflammatory demyelinating polyneuropathy, chronic recurrent multifocal osteomyelitis, chronic obstructive pulmonary disease, chronic venous stasis ulcers, Churg-Strauss syndrome, cicatricial pemphigoid, Cogan syndrome, cold agglutinin disease, complement component 2 deficiency, contact dermatitis, cranial arteritis, CREST syndrome, Crohn's disease, Cushing's Syndrome, cutaneous leukocytoclastic angiitis, Dego's disease, Dercum's disease, dermatitis herpetiformis, dermatomyositis, Diabetes mellitus type I, Diabetes mellitus type II diffuse cutaneous systemic sclerosis, Dressler's syndrome, drug-induced lupus, discoid lupus erythematosus, eczema, emphysema, endometriosis, enthesitis-related arthritis, eosinophilic fasciitis, eosinophilic gastroenteritis, eosinophilic pneumonia, epidermolysis bullosa acquisita, erythema nodosum, erythroblastosis fetalis, essential mixed cryoglobulinemia, Evan's syndrome, fibrodysplasia ossificans progressive, fibrosing alveolitis (or idiopathic pulmonary fibrosis), gastritis, gastrointestinal pemphigoid, Gaucher's disease, glomerulonephritis, Goodpasture's syndrome, Graves' disease, Guillain-Barré syndrome (GBS), Hashimoto's encephalopathy, Hashimoto's thyroiditis, heart disease, Henoch-Schonlein purpura, herpes gestationis (aka gestational pemphigoid), hidradenitis suppurativa, HIV infection, Hughes-Stovin syndrome, hypogammaglobulinemia, infectious diseases (including bacterial infectious diseases), idiopathic inflammatory demyelinating diseases, idiopathic pulmonary fibrosis, idiopathic thrombocytopenic purpura, IgA nephropathy, inclusion body myositis, inflammatory arthritis, inflammatory bowel disease, inflammatory dementia, interstitial cystitis, interstitial pneumonitis, juvenile idiopathic arthritis (aka juvenile rheumatoid arthritis), Kawasaki's disease, Lambert-Eaton myasthenic syndrome, leukocytoclastic vasculitis, lichen planus, lichen sclerosus, linear IgA disease (LAD), lupoid hepatitis (aka autoimmune hepatitis), lupus erythematosus, lymphomatoid granulomatosis, Majeed syndrome, malignancies including cancers (e.g., sarcoma, Kaposi's sarcoma, lymphoma, leukemia, carcinoma and melanoma), Meniere's disease, microscopic polyangiitis, Miller-Fisher syndrome, mixed connective tissue disease, morphea, Mucha-Habermann disease (aka *Pityriasis lichenoides* et varioliformis acuta), multiple sclerosis, myasthenia gravis, myositis, narcolepsy, neuromyelitis optica (aka Devic's disease), neuromyotonia, occular cicatricial pemphigoid, opsoclonus myoclonus syndrome, Ord's thyroiditis, palindromic rheumatism, PANDAS (pediatric autoimmune neuropsychiatric disorders associated with *Streptococcus*), paraneoplastic cerebellar degeneration, Parkinsonian disorders, paroxysmal nocturnal hemoglobinuria (PNH), Parry Romberg syndrome, Parsonage-Turner syndrome, pars planitis, pemphigus vulgaris, peripheral artery disease, pernicious anaemia, perivenous encephalomyelitis, POEMS syndrome, polyarteritis nodosa, polymyalgia rheumatic, polymyositis, primary biliary cirrhosis, primary sclerosing cholangitis, progressive inflammatory neuropathy, psoriasis, psoriatic arthritis, pyoderma gangrenosum, pure red cell aplasia, Rasmussen's encephalitis, Raynaud phenomenon, relapsing polychondritis, Reiter's syndrome, restenosis, restless leg syndrome, retroperitoneal fibrosis, rheumatoid arthritis, rheumatic fever, sarcoidosis, schizophrenia, Schmidt syndrome, Schnitzler syndrome, scleritis, scleroderma, sepsis, serum Sickness, Sjögren's syndrome, spondyloarthropathy, Still's disease (adult onset), stiff person syndrome, stroke, subacute bacterial endocarditis (SBE), Susac's syndrome, Sweet's syndrome, Sydenham chorea, sympathetic ophthalmia, systemic lupus erythematosus, Takayasu's arteritis, temporal arteritis (aka "giant cell arteritis"), thrombocytopenia, Tolosa-Hunt syndrome) transplant (e.g., heart/lung transplants) rejection reactions, transverse myelitis, tuberculosis, ulcerative colitis, undifferentiated connective tissue disease, undifferentiated spondyloarthropathy, urticarial vasculitis, vasculitis, vitiligo, and Wegener's granulomatosis.

Kits

Also provided herein are kits of pharmaceutical formulations containing the disclosed compounds or compositions. The kits may be organized to indicate a single formulation or combination of formulations. The composition may be sub-divided to contain appropriate quantities of the compound. The unit dosage can be packaged compositions such as packeted powders, vials, ampoules, prefilled syringes or sachets containing liquids.

The compound or composition described herein may be a single dose or for continuous or periodic discontinuous administration. For continuous administration, a kit may include a compound in each dosage unit. For periodic discontinuation, the kit may include placebos during periods when the compound is not delivered. When varying concentrations of the composition, the components of the composition, or relative ratios of the compound or other agents within a composition over time is desired, a kit may contain a sequence of dosage units.

The kit may contain packaging or a container with the compound formulated for the desired delivery route. The kit may also contain dosing instructions, an insert regarding the compound, instructions for monitoring circulating levels of the compound, or combinations thereof. Materials for performing using the compound may further be included and include, without limitation, reagents, well plates, containers, markers or labels, and the like. Such kits are packaged in a manner suitable for treatment of a desired indication. Other suitable components to include in such kits will be readily apparent to one of skill in the art, taking into consideration the desired indication and the delivery route. The kits also may include, or be packaged with, instruments for assisting with the injection/administration or placement of the compound within the body of the subject. Such instruments include, without limitation, an inhalant, syringe, pipette, forceps, measuring spoon, eye dropper or any such medically approved delivery means. Other instrumentation may include a device that permits reading or monitoring reactions in vitro.

The compound or composition of these kits also may be provided in dried, lyophilized, or liquid forms. When reagents or components are provided as a dried form, reconstitution generally is by the addition of a solvent. The solvent may be provided in another packaging means and may be selected by one skilled in the art.

A number of packages or kits are known to those skilled in the art for dispensing pharmaceutical agents. In one embodiment, the package is a labeled blister package, dial dispenser package, or bottle.

In certain aspects, the kit disclosed herein includes a blocking compound; a mannosylated carbohydrate polymeric therapeutic or diagnostic compound comprising a dextran backbone and one or more CD206 targeting moieties and one or more therapeutic agents attached thereto; and wherein the net charge of the blocking compound is opposite of that of the mannosylated carbohydrate polymeric therapeutic or diagnostic compound. In additional embodiments, the kit disclosed herein includes a charged mannosylated carbohydrate polymeric therapeutic or diagnostic compound comprising a dextran backbone and one or more CD206 targeting moieties and one or more therapeutic agents attached thereto without the inclusion of a blocking compound.

In certain aspects, the blocking compound is a charged compound. In additional aspects, the blocking compound comprises a backbone and one or more CD206 targeting moieties attached thereto. In certain aspects, the kit includes a mannosylated carbohydrate polymeric therapeutic or diagnostic compound having a compound of Formula (I) and a blocking compound of Formula (II):

(I)

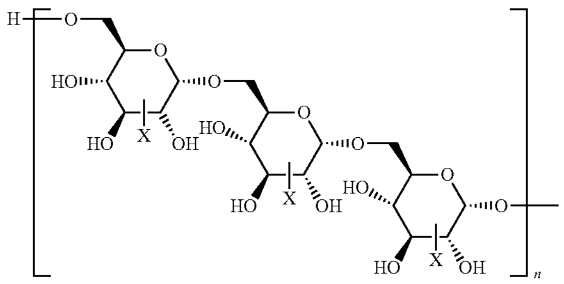

wherein each X is independently H, L1-A, L2-R, L3-W, or L4-A-W;

each L1, L2, L3, and L4 are independently leashes;

each A independently comprises a therapeutic agent, a diagnostic agent, or H;

each R independently comprises a mannose-binding C-type lectin receptor targeting moiety or H;

each W is independently a terminal amine group comprising a linear or branched polyamine, guanidine, or quaternary ammonium moiety;

and n is an integer greater than zero; wherein each unit of n may be the same or different; and wherein at least one R comprises a mannose-binding C-type lectin receptor targeting moiety selected from the group consisting of mannose, galactose, fucose, N-acetylgalactosamine (GalNAc), N-acetylglucosamine (GlcNAc), and/or glucuronic acid and at least one A comprises a therapeutic agent or diagnostic agent; and (II)

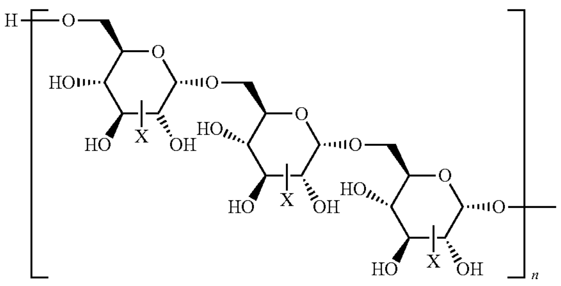

wherein each X is H, L1-R, or L2-Y;

each L1 and L2 are independently leashes;

each R independently comprises a mannose-binding C-type lectin receptor targeting moiety or H; and each Y independently comprises a carboxylate, sulfate, sulfonate, sulfinate, phosphate, phosphonate, phosphinate, or mannose moiety, or H; and n is an integer greater than zero, wherein each unit of n may be the same or different.

All publications and patent applications in this specification are indicative of the level of ordinary skill in the art to which this invention pertains. All publications and patent applications are herein incorporated by reference to the same extent as if each individual publication or patent application was specifically and individually indicated as incorporated by reference.

EXAMPLES

The following examples are put forth so as to provide those of ordinary skill in the art with a complete disclosure and description of certain examples of how the compounds, compositions, articles, devices and/or methods claimed herein are made and evaluated and are intended to be purely exemplary of the disclosure and are not intended to limit the scope of what the inventors regard as their invention. However, those of skill in the art should, in light of the present disclosure, appreciate that many changes can be made in the specific embodiments which are disclosed and still obtain a like or similar result without departing from the spirit and scope of the disclosure.

Example 1

Anionic Carboxylic Dextran Synthesis

Figure 1B:
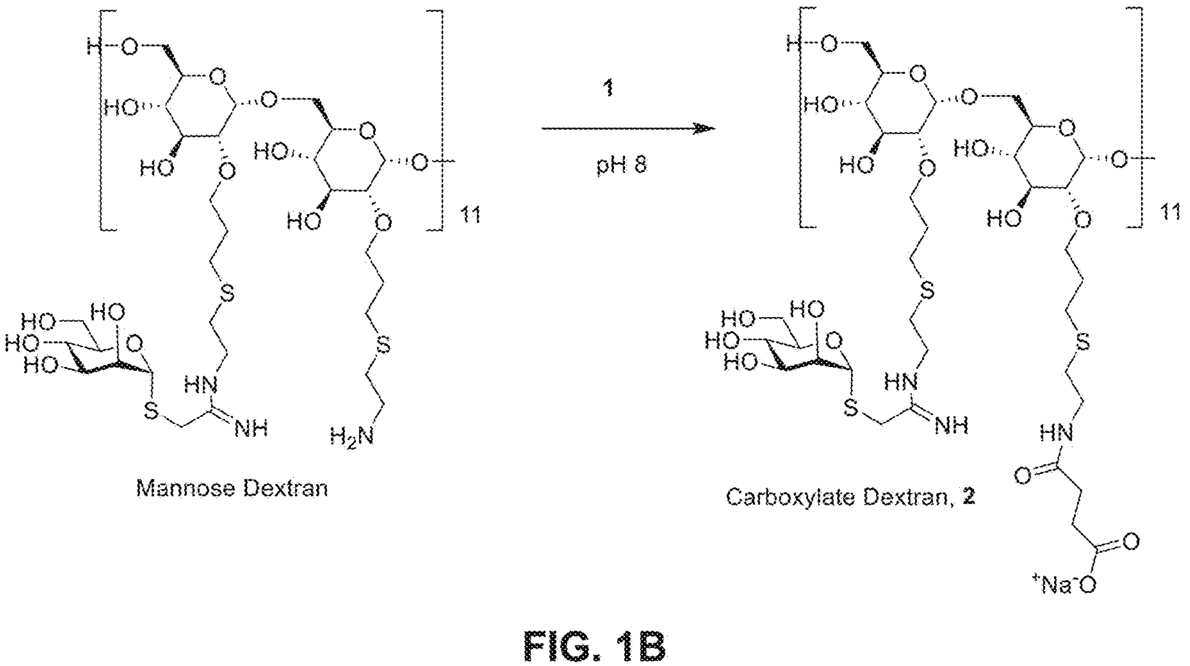
FIG. 1B shows a reaction scheme of a mannose dextran to a carboxylate dextran 2.

Anionic carboxylic dextrans were synthesized in the following manner provided within this example. The synthesis scheme as referenced throughout the example is shown in FIG. 1A and FIG. 1B. Carboxylate dextran 2 was synthesized by reaction of succinimidyl succinate 1 with mannose amino dextran (MAD) in aqueous pH 8 buffer. NHS ester 1 was prepared by slight modification of the method reported by Loomans, E. M. G; et al. *J. Agric. Food Chem.,* 2003, 51(3), 587-593. 200 mg (2.0 mmol) of succinic anhydride was combined with 10 ml of dry dichloromethane and heated briefly under nitrogen until the anhydride was dissolved. The solution was cooled to room temperature and 230 mg (2.0 mmol) of N-hydroxysuccinimide was added and sonicated briefly providing a clear solution. The solution was removed from the sonicator and 0.33 ml (2.4 mmol) of triethylamine was added. After 3 hours of stirring at room temperature, the reaction was diluted with ethyl acetate and washed twice with ice cold 1 N HCl. The organics were dried over anhydrous sodium sulfate, filtered, concentrated, and placed on hi-vacuum. The white solid 1 material (128 mg, 30%), was consistent by 1H NMR and used without further purification in the coupling reaction.

The conversion of MAD to anionic carboxylate dextran 2 was conducted on 50 mg scale (6.2 umol) by dissolving 11-mannose 6-amine dextran in 2 ml of 0.1M pH 8.2 sodium carbonate and adding 50 mg of the crude NHS-ester 1. At 1 hour of reaction, negligible fluorescence was detected compared to an equivalent quantity of the starting MAD by fluorescamine assay, indicating the available amines on the MAD construct had been derivatized to amides. The material was concentrated and washed with water via 3 kDa MWCO ultracentrifuge filters, passed through a 0.2 um filter, frozen and lyophilized. 47 mg of dry lyophilizate 2 was isolated and was consistent by 1H and 13C (new signals included 178.75 ppm and 165.28 ppm) NMR in $D_2O$.

Example 2

Anionic Sulfonate Dextran Synthesis

Figure 2A:
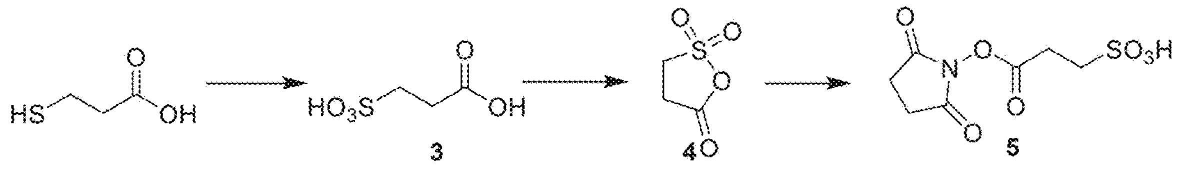
FIG. 2A shows a reaction scheme in preparing NHS ester 5 from three separate steps.
Figure 2B:
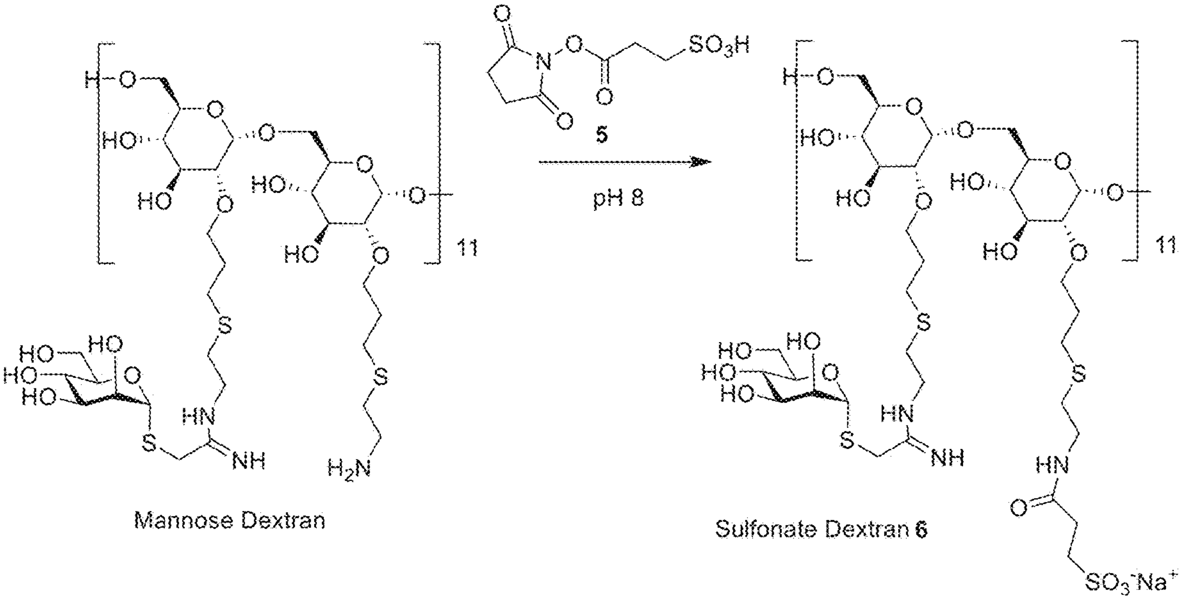
FIG. 2B shows a reaction scheme of a mannose dextran to a sulfonate dextran 6.

Anionic sulfonate dextrans were synthesized in the following manner provided within this example. The synthesis schemes as referenced throughout the example is shown in FIG. 2A and FIG. 2B. Sulfonate dextran 6 was synthesized by reaction of the NHS ester 5 with mannose amino dextran (MAD) in aqueous pH 8 buffer. NHS ester 5 was prepared in three steps as described in WO 02/095412, the contents of which is hereby incorporated by reference. 2.9 ml of 30% hydrogen peroxide and 10 ml of glacial acetic were charged to a flask fitted with a cold-water condenser. The solution was warmed on an oil bath to 35° C. and 1.0 g (9.4 mmol) of 3-mercaptopropionic acid was added dropwise. The internal reaction temperature increased slowly to 60° C. (use caution-rapid exotherm is observed at 10 g scale) and the oil bath temperature was increased to 90° C. for 30 minutes after the internal reaction temperature was stabilized. The reaction was removed from the oil bath, allowed to equilibrate to ambient temperature, concentrated two times with hexanes and placed on hi-vacuum for >24 hours. Using oven-dried glassware and nitrogen atmosphere for all steps, the conversion of crude 3 to the water sensitive sulfopropionic anhydride 4 was conducted by refluxing the crude sulfonic acid 3 for 3 hours in 11 ml of thionyl chloride under a cold-water condenser. The reaction was cooled, precipitated by addition of 10 ml of hexanes, heated to re-dissolve and decanted, taking care to leave behind a dark brown oil by-product. The product in the filtrate was allowed to cool to room temperature and then −20° C. to crystallize o/n. 418 mg of light brown solid 4 was obtained after filtration under nitrogen, washing with ice-cold hexanes, and placement on hi-vacuum for 20 hours.

400 mg of crude anhydride 4 was dissolved in 16 ml of dry dichloromethane with an approximate equivalent each of N-hydroxysuccinimide (338 mg, 2.94 mmol) and diisopropylethyl amine (512 ul, 2.94 mmol) and stirred at room temperature under nitrogen atmosphere. After 3 hours, the clear amber reaction solution was concentrated and placed on hi-vacuum. The resulting crude amber oil 5 was consistent as the diisopropylethylamine salt by 1H NMR and was used without further purification in the coupling reaction.

The conversion of MAD to anionic sulfonate dextran 6 was conducted on 15 mg scale (1.8 μmol) by dissolving 11-mannose 6-amine dextran in 0.6 ml of 0.1M pH 8.2 sodium carbonate followed by the addition of crude NHS-ester 5 until negligible fluorescence was detected compared to an equivalent quantity of the starting MAD by fluorescamine assay. This indicated that the available amines on the MAD construct had been consumed by derivatization to amides. The material was concentrated and washed with water via 3 kDa MWCO, ultracentrifuge filters, passed through a 0.2 μm filter, frozen and lyophilized. 12 mg of dry lyophilizate 6 was isolated and consistent by 1H and 13C (new signals included 165.28 ppm) NMR in $D_2O$.

Although the disclosure has been described with references to various embodiments, persons skilled in the art will recognize that changes may be made in form and detail without departing from the spirit and scope of this disclosure.

What is claimed is:

1. A composition comprising:

a blocking compound comprising the compound of Formula (II)

(II)

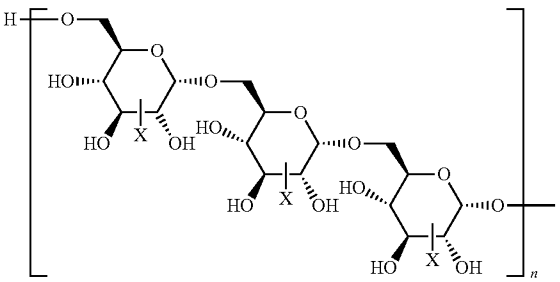

wherein each X is independently H, L1-R, or L2-Y;

each L1 and L2 are independently leashes, wherein each of L1 and L2 independently comprise the formula $—(CH_2)_pS(CH_2)_q—NH—$, wherein p and q are integers from 0 to 5;

each R independently comprises a mannose-binding C-type lectin receptor targeting moiety or H;

each Y independently comprises a carboxylate, sulfate, sulfonate, sulfinate, phosphate, phosphonate, phosphinate, or mannose moiety, or H; and n is an integer greater than zero, wherein each unit of n may be the same or different; and wherein at least one R comprises a mannose-binding C-type lectin receptor targeting moiety selected from the group consisting of mannose, galactose, fucose, N-acetylgalactosamine (GalNAc), N-acetylglucosamine (GlcNAc), and glucuronic acid; and wherein at least one Y comprises a carboxylate, sulfate, sulfonate, sulfinate, phosphate, phosphonate, phosphinate, or mannose moiety;

a mannosylated carbohydrate polymeric therapeutic or diagnostic compound comprising the compound of Formula (I)

(I)

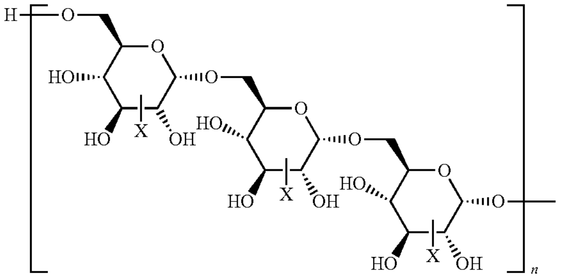

wherein each X is independently H, L1-A, L2-R, L3-W, or L4-A-W;

each L1, L2, L3, and L4 are independently leashes, wherein each of L1, L2, and L4 independently comprise the formula $—(CH_2)_pS(CH_2)_q—NH—$, wherein p and q are integers from 0 to 5, and wherein each L3 independently comprises the formula $—(CH_2)_pS(CH_2)_q—$, wherein p and q are integers from 0 to 5;

each A independently comprises a therapeutic agent, a diagnostic agent, or H;

each R independently comprises a mannose-binding C-type lectin receptor targeting moiety or H;

each W is independently a terminal amine group comprising a linear or branched polyamine, guanidine, or quaternary ammonium moiety; and n is an integer greater than zero, wherein each unit of n may be the same or different; and wherein at least one R comprises a mannose-binding C-type lectin receptor targeting moiety selected from the group consisting of mannose, galactose, fucose, N-acetylgalactosamine (GalNAc), N-acetylglucosamine (GlcNAc), and glucuronic acid; and at least one A comprises a therapeutic agent or diagnostic agent;

wherein at least one X is L3-W or L4-A-W;

wherein the blocking compound is polyanionic and thereby negatively charged, or neutral; and wherein the mannosylated carbohydrate polymeric therapeutic or diagnostic compound is polycationic and thereby positively charged.

2. The composition of claim 1, wherein at least one Y is a carboxylate or sulfonate moiety.

3. The composition of claim 1, wherein the blocking compound backbone has a molecular weight of from about 1 kDa to about 500 kDa, and the mannosylated carbohydrate polymeric therapeutic or diagnostic compound dextran backbone has a molecular weight of from about 1 kDa to about 20 kDa.

4. A method of increasing target specificity of a mannosylated carbohydrate polymeric therapeutic or diagnostic compound in a subject comprising:

administering a composition according to claim 1 to the subject wherein the blocking compound is polyanionic and thereby negatively charged, or neutral; and wherein the mannosylated carbohydrate polymeric therapeutic or diagnostic compound is polycationic and thereby positively charged.

5. The method of claim 4, wherein the method reduces or eliminates localization of the mannosylated carbohydrate polymeric therapeutic or diagnostic compound to off-target sites comprising the liver, the kidney, and/or the spleen of the subject.

6. The method of claim 4, wherein when at least one Y is the mannose moiety, each Y within formula (II) must be the mannose moiety.

7. The method of claim 4, wherein the blocking compound does not contain a therapeutic or diagnostic agent.

8. The method of claim 4, wherein the blocking compound backbone has a molecular weight of from about 1 kDa to about 500 kDa, and the mannosylated carbohydrate polymeric therapeutic or diagnostic compound dextran backbone has a molecular weight of from about 1 kDa to about 20 kDa.

9. The method of claim 4, wherein the step of administering the blocking compound is followed by a time interval of 0 to about 60 minutes before the step of administering the mannosylated carbohydrate polymeric therapeutic or diagnostic compound.

10. The method of claim 4, wherein the blocking compound and the mannosylated carbohydrate polymeric therapeutic or diagnostic compound are administered simultaneously.

11. The method of claim 4, wherein the mannosylated carbohydrate polymeric therapeutic or diagnostic compound comprises the one or more therapeutic agents.

12. The method of claim 4, wherein the portion of the administered dose of the mannosylated carbohydrate polymeric therapeutic or diagnostic compound that localizes to a desired target tissue other than the liver, kidney, and/or spleen is higher than the localizing portion of the mannosylated carbohydrate polymeric therapeutic or diagnostic compound without administration of the blocking compound.

13. The method of claim 4, wherein the effective dose of the mannosylated carbohydrate polymeric therapeutic or diagnostic compound is lower than the effective does of the mannosylated carbohydrate polymeric therapeutic or diagnostic compound without administration of the blocking compound.

14. The method of claim 4, wherein the blocking compound preferentially binds to CD206 expressing cells in the liver, kidney, and/or spleen.

15. The method of claim 4, wherein the mannosylated carbohydrate polymeric therapeutic or diagnostic compound has decreased binding to CD206 cells in the liver, kidney, and/or spleen relative to a subject administered a comparable dose of mannosylated carbohydrate polymeric therapeutic or diagnostic compound without administration of the blocking compound.

16. The method of claim 4, wherein the subject has been diagnosed with an autoimmune disease, an inflammatory disease, or cancer.

* * * * *